United States Patent
Fowler et al.

(10) Patent No.: US 8,929,991 B2
(45) Date of Patent: *Jan. 6, 2015

(54) METHODS FOR ESTABLISHING PARAMETERS FOR NEURAL STIMULATION, INCLUDING VIA PERFORMANCE OF WORKING MEMORY TASKS, AND ASSOCIATED KITS

(75) Inventors: Brad Fowler, Duvall, WA (US); Leif R. Sloan, Seattle, WA (US); Joleen Borgerding, Seattle, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 2150 days.

This patent is subject to a terminal disclaimer.

(21) Appl. No.: 11/737,673

(22) Filed: Apr. 19, 2007

(65) Prior Publication Data

US 2007/0265489 A1 Nov. 15, 2007

Related U.S. Application Data

(63) Continuation-in-part of application No. 11/254,240, filed on Oct. 19, 2005, now abandoned.

(51) Int. Cl.
*A61N 1/36* (2006.01)
*A61N 1/05* (2006.01)

(52) U.S. Cl.
CPC ........ *A61N 1/36082* (2013.01); *A61N 1/36096* (2013.01); *A61N 1/0531* (2013.01); *A61N 1/0534* (2013.01)
USPC .......................................................... 607/45

(58) Field of Classification Search
CPC ................................................. A61N 1/36096
USPC .......................................................... 607/45
See application file for complete search history.

(56) References Cited

U.S. PATENT DOCUMENTS

| 2,716,226 A | 8/1955 | Jonas |
| 2,721,316 A | 10/1955 | Shaw |

(Continued)

FOREIGN PATENT DOCUMENTS

| DE | 19750043 | 5/1999 |
| EP | 0214527 | 3/1987 |

(Continued)

OTHER PUBLICATIONS

U.S. Appl. No. 10/583,630, filed Jun. 20, 2006, Lozano.

(Continued)

*Primary Examiner* — Eric D. Bertram

(57) ABSTRACT

Methods for establishing parameters for neural stimulation, including via performance of working memory tasks, and associated kits, are disclosed. A method in accordance with one embodiment includes engaging a patient in a function controlled at least in part by a target neural population, and applying electromagnetic signals to the target neural population. A target parameter in accordance with which the electromagnetic signals are applied is adjusted, based at least in part on a characteristic of the patient's performance of the function. Electromagnetic signals are applied to the patient with the adjusted target parameter, and the patient's response to the electromagnetic signals, including the characteristic of the patient's performance, is evaluated. Based at least in part on the evaluation of the patient's response, an embodiment of the method includes determining whether to apply further electromagnetic signals to the patient, establishing a value of the target parameter for applying further electromagnetic signals to the patient, and/or adjusting another target parameter in accordance with which the electromagnetic signals are applied to the patient.

38 Claims, 13 Drawing Sheets

(56) References Cited

U.S. PATENT DOCUMENTS

| | | |
|---|---|---|
| 3,628,193 A | 12/1971 | Collins |
| 3,650,276 A | 3/1972 | Burghele et al. |
| 3,850,161 A | 11/1974 | Liss |
| 3,918,461 A | 11/1975 | Cooper |
| 4,030,509 A | 6/1977 | Heilman et al. |
| 4,125,116 A | 11/1978 | Fischell |
| 4,140,133 A | 2/1979 | Kastrubin et al. |
| 4,214,804 A | 7/1980 | Little |
| 4,245,645 A | 1/1981 | Arseneault et al. |
| 4,308,868 A | 1/1982 | Jhabvala |
| 4,328,813 A | 5/1982 | Ray |
| 4,340,038 A | 7/1982 | McKean |
| 4,431,000 A | 2/1984 | Butler et al. |
| 4,474,186 A | 10/1984 | Ledley et al. |
| 4,542,752 A | 9/1985 | Dehaan et al. |
| 4,590,946 A | 5/1986 | Loeb |
| 4,607,639 A | 8/1986 | Tanagho et al. |
| 4,646,744 A | 3/1987 | Capel |
| 4,702,254 A | 10/1987 | Zabara |
| 4,844,075 A | 7/1989 | Liss et al. |
| 4,865,048 A | 9/1989 | Eckerson |
| 4,869,255 A | 9/1989 | Putz |
| 4,903,702 A | 2/1990 | Putz |
| 4,940,453 A * | 7/1990 | Cadwell ..................... 600/13 |
| 4,969,468 A | 11/1990 | Byers et al. |
| 5,002,053 A | 3/1991 | Garcia-Rill et al. |
| 5,024,226 A | 6/1991 | Tan |
| 5,031,618 A | 7/1991 | Mullett |
| 5,044,368 A | 9/1991 | Putz |
| 5,054,906 A | 10/1991 | Lyons |
| 5,063,932 A | 11/1991 | Dahl et al. |
| 5,092,835 A | 3/1992 | Schurig et al. |
| 5,121,754 A | 6/1992 | Mullett |
| 5,143,089 A | 9/1992 | Alt |
| 5,169,384 A | 12/1992 | Bosniak et al. |
| 5,184,620 A | 2/1993 | Cudahy et al. |
| 5,193,540 A | 3/1993 | Schulman et al. |
| 5,215,086 A | 6/1993 | Terry, Jr. et al. |
| 5,215,088 A | 6/1993 | Normann et al. |
| 5,224,491 A | 7/1993 | Mehra |
| 5,255,678 A | 10/1993 | Deslauriers et al. |
| 5,263,967 A | 11/1993 | Lyons, III et al. |
| 5,269,303 A | 12/1993 | Wernicke et al. |
| 5,271,417 A | 12/1993 | Swanson et al. |
| 5,282,468 A | 2/1994 | Klepinski |
| 5,299,569 A | 4/1994 | Wernicke et al. |
| 5,303,705 A | 4/1994 | Nenov |
| 5,304,206 A | 4/1994 | Baker, Jr. et al. |
| 5,314,458 A | 5/1994 | Najafi et al. |
| 5,358,513 A | 10/1994 | Powell, III et al. |
| 5,370,672 A | 12/1994 | Fowler et al. |
| 5,405,375 A | 4/1995 | Ayers et al. |
| 5,406,957 A | 4/1995 | Tansey |
| 5,411,540 A | 5/1995 | Edell et al. |
| 5,417,719 A | 5/1995 | Hull et al. |
| 5,423,864 A | 6/1995 | Ljungstroem |
| 5,441,528 A | 8/1995 | Chang et al. |
| 5,464,446 A | 11/1995 | Dreessen et al. |
| 5,520,190 A | 5/1996 | Benedict et al. |
| 5,522,864 A | 6/1996 | Wallace et al. |
| 5,537,512 A | 7/1996 | Hsia et al. |
| 5,540,734 A | 7/1996 | Zabara |
| 5,540,736 A | 7/1996 | Haimovich et al. |
| 5,549,655 A | 8/1996 | Erickson |
| 5,562,708 A | 10/1996 | Combs et al. |
| 5,575,813 A | 11/1996 | Edell et al. |
| 5,591,216 A | 1/1997 | Testerman et al. |
| 5,593,432 A | 1/1997 | Crowther et al. |
| 5,601,611 A | 2/1997 | Fayram et al. |
| 5,611,350 A | 3/1997 | John |
| 5,618,531 A | 4/1997 | Cherksey |
| 5,628,317 A | 5/1997 | Starkebaum et al. |
| 5,674,251 A | 10/1997 | Combs et al. |
| 5,676,655 A | 10/1997 | Howard, III et al. |
| 5,683,422 A | 11/1997 | Rise |
| 5,702,429 A | 12/1997 | King |
| 5,707,334 A | 1/1998 | Young |
| 5,711,316 A | 1/1998 | Elsberry et al. |
| 5,713,922 A | 2/1998 | King |
| 5,713,923 A | 2/1998 | Ward et al. |
| 5,716,377 A | 2/1998 | Rise et al. |
| 5,722,401 A | 3/1998 | Pietroski |
| 5,735,814 A | 4/1998 | Elsberry et al. |
| 5,750,376 A | 5/1998 | Weiss et al. |
| 5,752,979 A | 5/1998 | Benabid |
| 5,769,778 A | 6/1998 | Abrams et al. |
| 5,772,591 A | 6/1998 | Cram |
| 5,782,798 A | 7/1998 | Rise |
| 5,782,873 A | 7/1998 | Collins |
| 5,792,186 A | 8/1998 | Rise |
| 5,797,970 A | 8/1998 | Pouvreau |
| 5,814,014 A | 9/1998 | Elsberry et al. |
| 5,814,092 A | 9/1998 | King |
| 5,824,021 A | 10/1998 | Rise |
| 5,824,030 A | 10/1998 | Yang et al. |
| 5,832,932 A | 11/1998 | Elsberry et al. |
| 5,833,709 A | 11/1998 | Rise et al. |
| 5,843,148 A | 12/1998 | Gijsbers et al. |
| 5,843,150 A | 12/1998 | Dreessen et al. |
| 5,865,842 A | 2/1999 | Knuth et al. |
| 5,871,517 A | 2/1999 | Abrams et al. |
| 5,885,976 A | 3/1999 | Sandyk |
| 5,886,769 A | 3/1999 | Zolten |
| 5,893,883 A | 4/1999 | Torgerson et al. |
| 5,904,916 A | 5/1999 | Hirsch |
| 5,913,882 A | 6/1999 | King |
| 5,916,171 A | 6/1999 | Mayevsky |
| 5,925,070 A | 7/1999 | King et al. |
| 5,928,144 A | 7/1999 | Real |
| 5,938,688 A | 8/1999 | Schiff |
| 5,938,689 A | 8/1999 | Fischell et al. |
| 5,941,906 A | 8/1999 | Barreras, Sr. et al. |
| 5,964,794 A | 10/1999 | Bolz et al. |
| 5,975,085 A | 11/1999 | Rise |
| 5,978,702 A | 11/1999 | Ward et al. |
| 5,983,140 A | 11/1999 | Smith et al. |
| 6,006,124 A | 12/1999 | Fischell et al. |
| 6,011,996 A | 1/2000 | Gielen et al. |
| 6,016,449 A | 1/2000 | Fischell et al. |
| 6,018,682 A | 1/2000 | Rise |
| 6,021,352 A | 2/2000 | Christopherson et al. |
| 6,026,326 A | 2/2000 | Bardy |
| 6,035,236 A | 3/2000 | Jarding et al. |
| 6,040,180 A | 3/2000 | Johe |
| 6,042,579 A | 3/2000 | Elsberry et al. |
| 6,052,624 A | 4/2000 | Mann |
| 6,055,456 A | 4/2000 | Gerber |
| 6,057,846 A | 5/2000 | Sever, Jr. |
| 6,057,847 A | 5/2000 | Jenkins |
| 6,058,331 A | 5/2000 | King |
| 6,060,048 A | 5/2000 | Cherksey |
| 6,061,593 A | 5/2000 | Fischell et al. |
| 6,066,163 A | 5/2000 | John |
| 6,095,148 A | 8/2000 | Shastri et al. |
| 6,104,956 A | 8/2000 | Naritoku et al. |
| 6,104,960 A | 8/2000 | Duysens et al. |
| 6,122,548 A | 9/2000 | Starkebaum et al. |
| 6,126,657 A | 10/2000 | Edwards et al. |
| 6,128,527 A | 10/2000 | Howard, III et al. |
| 6,128,537 A | 10/2000 | Rise |
| 6,128,538 A | 10/2000 | Fischell et al. |
| 6,134,474 A | 10/2000 | Fischell et al. |
| 6,152,143 A | 11/2000 | Edwards |
| 6,161,044 A | 12/2000 | Silverstone |
| 6,161,045 A | 12/2000 | Fischell et al. |
| 6,176,242 B1 | 1/2001 | Rise |
| 6,190,893 B1 | 2/2001 | Shastri et al. |
| 6,198,958 B1 | 3/2001 | Ives et al. |
| 6,205,360 B1 | 3/2001 | Carter et al. |
| 6,210,417 B1 | 4/2001 | Baudino et al. |
| 6,221,908 B1 | 4/2001 | Kilgard et al. |
| 6,230,049 B1 | 5/2001 | Fischell et al. |
| 6,236,892 B1 | 5/2001 | Feler |
| 6,246,912 B1 | 6/2001 | Sluijter et al. |

(56) References Cited

U.S. PATENT DOCUMENTS

| | | | |
|---|---|---|---|
| 6,263,225 B1 | 7/2001 | Howard, III | |
| 6,280,462 B1 | 8/2001 | Hauser et al. | |
| 6,301,493 B1 | 10/2001 | Marro et al. | |
| 6,304,787 B1 | 10/2001 | Kuzma et al. | |
| 6,319,241 B1 | 11/2001 | King et al. | |
| 6,339,725 B1 | 1/2002 | Naritoku et al. | |
| 6,353,754 B1 | 3/2002 | Fischell et al. | |
| 6,354,299 B1 | 3/2002 | Fischell et al. | |
| 6,356,792 B1 | 3/2002 | Errico et al. | |
| 6,360,122 B1 | 3/2002 | Fischell et al. | |
| 6,366,813 B1 | 4/2002 | DiLorenzo | |
| 6,375,666 B1 | 4/2002 | Mische | |
| 6,405,079 B1 | 6/2002 | Ansarinia | |
| 6,418,344 B1 | 7/2002 | Rezai | |
| 6,427,086 B1 | 7/2002 | Fischell et al. | |
| 6,456,886 B1 | 9/2002 | Howard, III et al. | |
| 6,459,936 B2 | 10/2002 | Fischell et al. | |
| 6,463,328 B1 | 10/2002 | John | |
| 6,464,356 B1 | 10/2002 | Sabel et al. | |
| 6,466,822 B1 | 10/2002 | Pless | |
| 6,473,639 B1 | 10/2002 | Fischell et al. | |
| 6,480,743 B1 | 11/2002 | Kirkpatrick et al. | |
| 6,484,059 B2 | 11/2002 | Gielen | |
| 6,487,450 B1 | 11/2002 | Chen | |
| 6,499,488 B1 | 12/2002 | Hunter et al. | |
| 6,505,075 B1 | 1/2003 | Weiner | |
| 6,507,755 B1 | 1/2003 | Gozani et al. | |
| 6,529,774 B1 | 3/2003 | Greene | |
| 6,539,263 B1 | 3/2003 | Schiff et al. | |
| 6,549,814 B1 | 4/2003 | Strutz et al. | |
| 6,556,868 B2 | 4/2003 | Naritoku et al. | |
| 6,569,654 B2 | 5/2003 | Shastri et al. | |
| 6,591,138 B1 | 7/2003 | Fischell et al. | |
| 6,597,954 B1 | 7/2003 | Fischell et al. | |
| 6,615,065 B1 | 9/2003 | Barrett et al. | |
| 6,622,048 B1 | 9/2003 | Mann et al. | |
| 6,633,780 B1 | 10/2003 | Berger | |
| 6,647,296 B2 | 11/2003 | Fischell et al. | |
| 6,658,299 B1 | 12/2003 | Dobelle | |
| 6,665,562 B2 | 12/2003 | Gluckman et al. | |
| 6,684,105 B2 | 1/2004 | Cohen et al. | |
| 6,687,525 B2 | 2/2004 | Llinas et al. | |
| 6,690,974 B2 | 2/2004 | Archer et al. | |
| 6,708,064 B2 | 3/2004 | Rezai | |
| 6,725,094 B2 | 4/2004 | Saberski | |
| 6,731,978 B2 | 5/2004 | Olson et al. | |
| 6,764,498 B2 | 7/2004 | Mische | |
| 6,782,292 B2 | 8/2004 | Whitehurst | |
| 6,788,975 B1 | 9/2004 | Whitehurst et al. | |
| 6,795,737 B2 | 9/2004 | Gielen et al. | |
| 6,810,286 B2 | 10/2004 | Donovan et al. | |
| 6,839,594 B2 | 1/2005 | Cohen et al. | |
| 6,873,872 B2 | 3/2005 | Gluckman et al. | |
| 6,892,097 B2 | 5/2005 | Holsheimer | |
| 6,895,280 B2 | 5/2005 | Meadows et al. | |
| 6,907,296 B1 | 6/2005 | Doan et al. | |
| 6,934,580 B1 | 8/2005 | Osorio et al. | |
| 6,944,497 B2 | 9/2005 | Stypulkowski | |
| 6,944,501 B1 | 9/2005 | Pless | |
| 6,959,215 B2 | 10/2005 | Gliner et al. | |
| 6,990,377 B2 | 1/2006 | Gliner et al. | |
| 7,006,859 B1 | 2/2006 | Osorio et al. | |
| 7,010,351 B2 | 3/2006 | Firlik et al. | |
| 7,024,247 B2 | 4/2006 | Gliner et al. | |
| 7,065,412 B2 | 6/2006 | Swoyer | |
| 7,107,097 B2 | 9/2006 | Stern et al. | |
| 7,107,104 B2 | 9/2006 | Keravel et al. | |
| 7,110,820 B2 | 9/2006 | Tcheng et al. | |
| 7,146,217 B2 | 12/2006 | Firlik | |
| 7,149,586 B2 | 12/2006 | Greenberg et al. | |
| 7,184,840 B2 | 2/2007 | Stolz et al. | |
| 2002/0099412 A1 | 7/2002 | Fischell et al. | |
| 2002/0138101 A1 | 9/2002 | Suda et al. | |
| 2002/0169485 A1 | 11/2002 | Pless et al. | |
| 2003/0074032 A1 | 4/2003 | Gliner | |
| 2003/0078633 A1 | 4/2003 | Firlik et al. | |
| 2003/0088274 A1 | 5/2003 | Gliner et al. | |
| 2003/0097161 A1 | 5/2003 | Firlik et al. | |
| 2003/0125786 A1 | 7/2003 | Gliner et al. | |
| 2003/0130706 A1 | 7/2003 | Sheffield et al. | |
| 2003/0176901 A1 | 9/2003 | May | |
| 2003/0187490 A1 | 10/2003 | Gliner | |
| 2003/0195602 A1 | 10/2003 | Boling | |
| 2004/0073270 A1 | 4/2004 | Firlik et al. | |
| 2004/0082847 A1 | 4/2004 | McDermott | |
| 2004/0088024 A1* | 5/2004 | Firlik et al. | 607/45 |
| 2004/0092809 A1 | 5/2004 | DeCharms | |
| 2004/0102828 A1 | 5/2004 | Lowry et al. | |
| 2004/0111127 A1 | 6/2004 | Gliner et al. | |
| 2004/0131998 A1 | 7/2004 | Marom et al. | |
| 2004/0138550 A1 | 7/2004 | Hartlep et al. | |
| 2004/0158298 A1 | 8/2004 | Gliner et al. | |
| 2004/0176831 A1 | 9/2004 | Gliner et al. | |
| 2004/0181263 A1 | 9/2004 | Balzer et al. | |
| 2004/0236388 A1 | 11/2004 | Gielen et al. | |
| 2004/0249422 A1 | 12/2004 | Gliner et al. | |
| 2005/0004620 A1 | 1/2005 | Singhal et al. | |
| 2005/0015129 A1 | 1/2005 | Mische | |
| 2005/0021104 A1 | 1/2005 | DiLorenzo | |
| 2005/0021105 A1 | 1/2005 | Firlik et al. | |
| 2005/0021106 A1 | 1/2005 | Firlik et al. | |
| 2005/0021107 A1 | 1/2005 | Firlik et al. | |
| 2005/0021118 A1 | 1/2005 | Genau et al. | |
| 2005/0033378 A1* | 2/2005 | Sheffield et al. | 607/45 |
| 2005/0070971 A1 | 3/2005 | Fowler et al. | |
| 2005/0075679 A1 | 4/2005 | Gliner et al. | |
| 2005/0075680 A1 | 4/2005 | Lowry et al. | |
| 2005/0096701 A1 | 5/2005 | Donovan et al. | |
| 2005/0113882 A1 | 5/2005 | Cameron et al. | |
| 2005/0119712 A1 | 6/2005 | Shafer | |
| 2005/0154425 A1 | 7/2005 | Boveja et al. | |
| 2005/0154426 A1 | 7/2005 | Boveja et al. | |
| 2005/0182453 A1 | 8/2005 | Whitehurst | |
| 2006/0015153 A1 | 1/2006 | Gliner et al. | |
| 2006/0064138 A1* | 3/2006 | Velasco et al. | 607/42 |
| 2006/0106430 A1 | 5/2006 | Fowler et al. | |
| 2006/0106431 A1 | 5/2006 | Wyler et al. | |
| 2006/0129205 A1 | 6/2006 | Boveja et al. | |
| 2006/0173522 A1 | 8/2006 | Osorio | |
| 2006/0217782 A1 | 9/2006 | Boveja et al. | |
| 2006/0241717 A1 | 10/2006 | Whitehurst et al. | |
| 2007/0032834 A1 | 2/2007 | Gliner et al. | |
| 2007/0060974 A1 | 3/2007 | Lozano | |
| 2007/0088403 A1 | 4/2007 | Wyler | |
| 2007/0088404 A1* | 4/2007 | Wyler et al. | 607/46 |
| 2007/0100398 A1 | 5/2007 | Sloan | |

FOREIGN PATENT DOCUMENTS

| | | |
|---|---|---|
| EP | 0319844 | 6/1989 |
| EP | 0998958 | 5/2000 |
| EP | 1145736 | 10/2001 |
| EP | 1180056 | 11/2003 |
| WO | WO 87-07511 | 12/1987 |
| WO | WO 94-07564 | 4/1994 |
| WO | WO 95-21591 | 8/1995 |
| WO | WO 97-45160 | 12/1997 |
| WO | WO 98-06342 | 2/1998 |
| WO | WO 01-97906 | 12/2001 |
| WO | WO 02-09811 | 2/2002 |
| WO | WO 02-36003 | 5/2002 |
| WO | WO 02-38031 | 5/2002 |
| WO | WO 02-38217 | 5/2002 |
| WO | WO 03-043690 | 5/2003 |
| WO | WO 03-082402 | 10/2003 |

OTHER PUBLICATIONS

U.S. Appl. No. 11/254,060, filed Oct. 19, 2005, Wyler.
U.S. Appl. No. 11/255,187, filed Oct. 19, 2005, Firlik.
U.S. Appl. No. 11/344,453, filed Jan. 30, 2006, Gliner.
U.S. Appl. No. 11/518,139, filed Sep. 7, 2006, Weinand.
U.S. Appl. No. 11/638,326, filed Dec. 12, 2006, Gliner et al.
U.S. Appl. No. 11/697,694, filed Apr. 6, 2007, Fowler.

(56) References Cited

OTHER PUBLICATIONS

U.S. Appl. No. 11/697,696, filed Apr. 6, 2007, Pascual-Leone.
U.S. Appl. No. 11/697,703, filed Apr. 6, 2007, Gaw.
Barr, Deborah et al., "Induction and Reversal of Long-Term Potentiation by Low-and High-Intensity Theta Pattern Stimulation," The Journal of Neuroscience, 15(7): pp. 5402-5410 (Jul. 1995).
Barres et al., "Proliferation of oligodendrocyte precursor cells depends on electrical activity in axons," Nature; Medical Research Council Developmental Neurobiology Programme, Department of Biology, University College, London, p. 258-260, (Jan. 21, 1993).
Behrens, T. et al., "Non-invasive mapping of connections between human thalamus and cortex using diffusion imaging," Nature neuroscience, vol. 6 No. 7, pp. 750-757 (Jul. 2003).
Bel, S. and Bauer, B.L., "Dorsal Column Stimulation (DCS): Cost to Benefit Analysis," Acta Neurochirurgica, Suppl. 52, pp. 121-123 (1991).
Benabid, A.L. et al., "Chronic electrical stimulation of the ventralis intermedius nucleus of the thalamus as a treatment of movement disorders," J. Neurosurg., Apr. 1997, 86(4); 737; http:--www.ncbi.nlm.nih.gov; [accessed Nov. 18, 2003].
Beveridge, J. A., "Use of Exogenous Electric Current in the Treatment of Delayed Lesions in Peripheral Nerves," Plastic and Reconstructive Surgery, Oct. 1988, vol. 82, No. 4, pp. 573-579.
Bezard et al., "Cortical Stimulation and Epileptic Seizure: A Study of the Potential Risk in Primates," Neurosurgery, vol. 45, No. 2, Aug. 1999, 346-350.
Binder, J. M.D., "Functional Magnetic Resonance Imaging: Language Mapping," Neurosurgery Clinics of North America, vol. 8, No. 3, Jul. 1997, pp. 383-392.
Bluestone, Avraham Y. et al., "Three-dimensional optical tomography of hemodynamics in the human head," Optics Express, vol. 9, No. 6, pp. 272-286 (Sep. 10, 2001).
Brain Electrical Stimulation to Enhance Recovery After Stroke, ClinicalTrials.gov, URL: http://www.clinicaltrials.gov/ct/show/NCT00085657?order=2 [Retrieved on Dec. 22, 2005].
Burnett, Mark G. et al., "Diffuse optical measurement of blood flow, blood oxygenation, and metabolism in a human brain during sensorimotor cortex activation," Optics Letters, vol. 29, No. 15, pp. 1766-1768 (Aug. 1, 2004).
Bury, Scott et al., "The Effects of Behavioral Demand on Motor Cortical and Cerebellar Structural Plasticity After Brain Injury in Adult Rats," http://www.mcmaster.ca-inabis98-schallert-bury0827-two.html#introduction, 2 pages [Retrieved on Mar. 1, 2003].
Butefisch et al., "Mechanisms of use-dependent plasticity in the human motor cortex," Proc. Natl. Acad. Sci. USA, vol. 97, No. 7, pp. 3661-3665 (Mar. 2000).
Canavero, S. and Paolotti, R., "Extradural Motor Cortex Stimulation for Advanced Parkinson's Disease: Case Report," Movement Disorders, 15(1):169-171, 2000.
Cao, Yue et al., "Cortical Language Activation in Stroke Patients Recovering From Aphasia With Functional MRI," Stroke, vol. 30, pp. 2331-2340, Nov. 1999.
Cheun et al., "Differentiation of a Stem Cell Line Toward a Neuronal Phenotype," Int. J. Devi. Neuroscience, vol. 9, No. 4, pp. 391-404 (1991).
Cicinelli et al., "Transcranial magnetic stimulation reveals an interhemispheric asymmetry of cortical inhibition in focal epilepsy," Neurophysiology, vol. 11, No. 4 Mar. 20, 2000, pp. 701-707.
Cincotta et al., "Reorganization of the motor cortex in a patient with congenital hemiparesis and mirror movements," Neurology, vol. 55, pp. 129-131 (2000).
Cincotta et al., "Suprathreshold 0.3 Hz repetitive TMS prolongs the cortical silent period: potential implications for therapeutic trials in epilepsy," Clinical Neurophysiology, vol. 114, 2003, pp. 1827-1833, Elsevier Ireland Ltd.
Classen et al., "Rapid Plasticity of Human Cortical Movement Representation Induced by Practice," The Journal of Neurophysiology, vol. 79, No. 2, pp. 1117-1123 (Feb. 1998).
CNN.com, Health, "Lab Zaps Strokes with Magnetic Pulses," http://www.cnn.com/2004/HEALTH/conditions/11/29/zapping.strokes.ap/, Nov. 29, 2004, 4 pages [Retrieved on Dec. 2, 2004].
Cohen et al., "Studies of Neuroplasticity With Transcranial Magnetic Stimulation," The Journal of Clinical Neurophysiology, vol. 15, No. 4 (1998).
Cramer et al., "Use of Functional MRI to Guide Decisions in a clinical Stroke Trial," Stroke, Journal of the American Heart Association, May 2005, pp. e50-e52, American Heart Association, Dallas TX.
Cramer, S.C. and Bastings, E.P., "Mapping clinically relevant plasticity after stroke," Neuropharmacology vol. 19, No. 5, pp. 842-851 (Apr. 2000).
Cytokines Web Clinical Significance, Cytokines Web, 2 pages, URL: http:--cmbi.bjmu.edu.cn-cmbidata-cgf-CGF_Database-cytweb-roles-index.html [Retrieved on Sep. 2, 2005].
Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).
De Ridder, Dirk et al., "Magnetic and electrical stimulation of the auditory cortex for intractable tinnitus," Journal Neurosurg., vol. 100, pp. 560-564, (Mar. 2004).
Di Lazzaro, V. et al., "Theta-burst repetitive transcranial magnetic stimulation suppresses specific excitatory circuits in the human motor cortex," Physiology in Press; published online on Apr. 21, 2005 as 10.1113-jphysiol.2005.087288.
Ding, Yuemin et al., "Neural Plasticity After Spinal Cord Injury," Current Pharmaceutical Design vol. 11, No. 11, pp. 1441-1450, Abstract Only, 1 page (Apr. 2005).
Duncan, Pamela W. et al., "Defining post-stroke recovery: implications for design and interpretation of drug trials," Neuropharmacology vol. 39, pp. 835-841 (2000).
Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam.
Feys et al., "Value of somatosensory and motor evoked potentials in predicting arm recovery after a stroke," (Oct. 1999).
Franzini et al., "Reversal of thalamic hand syndrome by long-term motor cortex stimulation," Journal of Neurosurgery 93:873-875 (2000).
Fregni et al., "Antiepileptic Effects of Repetitive Transcranial Magnetic Stimulation in Patients with Cortical Malformations: An EEG and Clinical Study," ASSFN Proceedings 2004, Stereotactic and Functional Neurosurgery, 2005, 83:57-62.
Fregni, Felipe et al., "Anodal Transcranial Direct Current Stimulation of Prefrontal Cortex Enhances Working Memory," Experimental Brain Research vol. 166, No. 1, pp. 23-30 (Sep. 2005).
Gladstone et al., "Enhancing Recovery after Stroke with Noradrenergic Pharmacotherapy: A New Frontier?," Can J. Neurol. Sci., vol. 27, No. 2 (May 2000).
Gordon et al., "Parameters for direct cortical electrical stimulation in the human: histopathologic confirmation," Electroencephalography and clinical Neurophysiology, vol. 75, pp. 371-377 (1990).
Hagemann, Georg et al., "Increased Long-Term Potentiation in the Surround of Experimentally Induced Focal Cortical Infarction," Annals of Neurology, vol. 44, No. 2, pp. 255-258 (Aug. 1998).
Haglund, Michael M. et al., "Optical imaging of epileptiform and functional activity in human cerebral cortex," Nature, Aug. 20, 1992, pp. 668-671, vol. 358, Nature Publishing Group.
Hayakawa, Toshiji et al., "Changes in Cerebral Oxygenation and Hemodynamics During Obstructive Sleep Apneas," Chest, vol. 109, pp. 916-921 (1996).
Hodge, Jr., C.J. and Boakye, M., "Biological Plasticity: The Future of Science in Neurosurgery," Neurosurgery, vol. 48, No. 1 (Jan. 2001).
Hoshi, Yoko et al., "Detection of dynamic changes in cerebral oxygenation coupled to neuronal function during mental work in a man," Neuroscience Letters, vol. 150, pp. 5-8 (1993).
Hoshino et al., "Application of multichannel near-infrared spectroscopic topography to physiological monitoring of the cortex during cortical mapping: technical case report," Surgical Neurology, vol. 64, pp. 272-275 (2005).

(56) References Cited

OTHER PUBLICATIONS

How Imagent™ Works. ISS Inc., http://www.iss.com-Products-imagent_fmri.html, 1 page [Retrieved on Oct. 14, 2005].
Huang, Ying-Zu et al., "Theta Burst Stimulation of the Human Motor Cortex," Neuron, vol. 45, pp. 201-206 (Jan. 20, 2005).
Hummel, Friedhelm et al., "Effects of non-invasive cortical stimulation on skilled motor function in chronic stroke," Brain Advance Access, pp. 1-10, (Jan. 5, 2005).
Imagent™ Functional Brain Imaging System, ISS, Inc., http://www.iss.com-Products-imagent.html, 2 pages [Retrieved on Oct. 14, 2005].
Imagent™ functional Near Infrared Imaging System (fNIRS) Brain Imaging Using Infrared Photons, ISS Inc., http://www.iss.com-products-imagent-Imagent.pdf, 8 pages [Retrieved on Oct. 14, 2005].
Ishibashi, Tomoko et al., "Astrocytes Promote Myelination in Response to Electrical Impulses," Neuron 49, pp. 823-832, (Mar. 16, 2006).
Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp. 571-577 (Dec. 2003).
Kauhanen et al., "Domains and Determinants of Quality of Life After Stroke Caused by Brain Infarction," Arch. Phys. Med. Rehabil., vol. 81, pp. 1541-1546 (Dec. 2000).
Kelly-Spratt, K. "Transfection of PC-12 cells: a model system for primary neuronal cells," Qiagen News, Customer application article, www.qiagen.com, Issue 4, 1998, 2 pages.
Keyvani, Kathy et al., "Suppression of proteasome C2 contralateral to ischemic lesions in rat brain," Brain Research, vol. 858, pp. 386-392, 2000.
Kilgard, Michael et al., "Cortical Map Reorganization Enabled by Nucleus Basalis Activity," Science, vol. 279 pp. 1714-1717 (Mar. 13, 1998).
Kimura, K. et al., "Electrically induced neurite outgrowth of PC12 cells on the electrode surface," Entrez PubMed, http://www.ncbi.nlm.nih.gov/entrez/query.fcgi?db=pubmed&cmd=Retrieve&dopt=Abstract, 1 page.
Kinoshita et al., "Electric cortical stimulation suppresses epileptic and background activities in neocortical epilepsy and mesial temporal lobe epilepsy," Clinical Neurophysiology, vol. 116, 2005, pp. 1291-1299, Elsevier Ireland Ltd.
Kopell et al., "The Continuing Evolution of Psychiatric Neurosurgery," CNS Spectrums, vol. 5, No. 10, pp. 20-31 (Oct. 2000).
Kossoff et al., "Effect of an External Responsive Neurostimulator on Seizures and Electrographic Discharges during Subdural Electrode Monitoring," Epilepsia 45(12):1560-1567, 2004, Blackwell Publishing, Inc.
Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56:634-639, 2004 Society of Biological Psychiatry.
Larson, John et al., "Reversal of LTP by theta frequency stimulation," Brain Research, 600: pp. 97-102 (1993).
Lazar, M. et al., "White Matter Tractography Using Diffusion Tensor Deflection," Human Brain Mapping, 18:306-321, (2003).
L-DOPA dyskinesias, BioChemistry of PD, http://www.mayo.edu-fdp-pd-info-dyskinesias.htm [Retrieved on Dec. 22, 2005].
Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).
Liepert et al., "Treatment-Induced Cortical Reorganization After Stroke in Humans," Stroke, 31:1210-1216 (2000).
Lutsep et al., "Safety of Cortical Stimulation in Patients with Hemiparetic Stroke," Oasis, Online Abstract Submission and Invitation System—Program Planner, International Stroke Conference 2005, 1 pages, American Stroke Association.

Malenka, R.C. and Nicoll, R.A., "Long-Term Potenetiation—A Decade of Progress?," Neuroscience, vol. 285, No. 5435, Issue of Sep. 17, 1999, pp. 1870-1874.
Mansur, C.G. et al., "A sham stimulation-controlled trial of rTMS of the unaffected hemisphere in stroke patients," Neurology, vol. 64, pp. 1802-1804 (2005).
Martin et al., "Transcranial Magnetic Stimulation as a Complementary Treatment for Aphasia," Semin Speech Language, vol. 25, pp. 181-191 (2004) Abstract Only—1 page.
Martinez et al., "Motor hand recovery after stroke Prognostic yield of early transcranial magnetic stimulation," Electromyography. Clin. Neurophysiology, vol. 39, pp. 405-410 (1999).
Mendonca, A.C., "Directly applied low intensity direct electric current enhances peripheral nerve regeneration in rats," Journal of Neuroscience Methods, 2003, vol. 129, pp. 183-190.
Meyerson, B.A. et al., "Motor Cortex Stimulation as Treatment of Trigeminal Neuropathic Pain", Acta Neurochirurgica Supplementum, vol. 58, pp. 150-153 (1993).
Misawa et al., "Low-frequency transcranial magnetic stimulation for epilepsia partialis continua due to cortical dysplasia," Journal of the Neurological Sciences, vol. 234, 2005, pp. 37-39.
Montgomery, "Thalamic Stimulation," Neuroscience Pathways, The Cleveland Clinic Foundation, 2 pages.
Motamedi et al., "Optimizing Parameters for Terminating Cortical Afterdischarges with Pulse Stimulation," Epilepsia 43(8):836-846, 2002, Blackwell Publishing, Inc.
Netz et al., "Reorganization of motor output in the non-affected hemisphere after stroke," Brain, 120, pp. 1579-1586 (1997).
Nitsche, M.A. and Paulus, W., "Excitability changes induced in the human motor cortex by weak transcranial direct current stimulation," The Journal of Physiology, vol. 527.3, pp. 663-639 (2000).
Nitsche, Michael A. et al. "Facilitation of Implicit Motor Learning by Weak Transcranial Direct Current Stimulation of the Primary Motor Cortex in the Human," Journal of Cognitive Neuroscience 15:4, pp. 619-626, 2003 Massachusetts Institute of Technology.
Nitsche, Michael A. et al., "Level of action of cathodal DC opographyn induced inhibition of the human motor cortex," Dec. 2, 2002, Clinical Neurophysiology 114 (2003) 600-604.
Nudo, Randolph J. et al., "Recovery after damage to motor cortical areas," Current Opinion in Neurobiology, vol. 9, Issue 6, pp. 740-747, Dec. 1, 1999.
Oliveri et al., "Paired transcranial magnetic stimulation protocols reveal a pattern of inhibition and facilitation in the human parietal cortex," The Journal of Physiology, 529.2, pp. 461-468 (2000).
Panchanathan, Sethuraman et al., "Rehabilitation of patients with hemispatial neglect using visual-haptic feedback in Virtual reality environment," http://www.public.asu.edu-~tmcdani-publications.htm, 5 pages [Retrieved on Dec. 22, 2005].
Pascual-Leone et al., "Study and Modulation of Human Cortical Excitability With Transcranial Magnetic Stimulation," Journal of Clinical Neurophysiology, 1998, vol. 15, No. 4, pp. 333-343.
Pascual-Leone et al., "Transcranial magnetic stimulation and neuroplasticity," Neurophycologia 37, pp. 207-217 (1999).
Paulus, W, "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.
Paulus, Walter, "Toward Establishing a Therapeutic Window for rTMS by Theta Burst Stimulation," Neuron, vol. 45, pp. 181-183 (Jan. 20, 2005).
Penn, Michael, "Stemming Parkinson's," On Wisconsin Alumni Magazine, Summer 2003, http://www.uwalurrini.com-onwisconsin-2003_summer-research.html, 1 page [Retrieved on Dec. 22, 2005].
Politis, M. J., "Mammalian Optic Nerve Regeneration Following the Application of Electric Fields," The Journal of Trauma, Nov. 1988, vol. 28, No. 11, pp. 1548-1552.
Price, J. et al., "Neurotransplantation in neurodegenerative disease: a survey of relevant issues in developmental neurobiology," Novartis Foundation Symposium 231, 2000, pp. 148-165, Wiley, Chichester, UK.
Rezai, "Neurostimulation," Neurological Research, vol. 22, No. 3 pp. 235-273 (Apr. 2000).

(56) References Cited

OTHER PUBLICATIONS

Robinson, Kenneth R., "The Responses of Cells to Electrical Fields: A Review," The Journal of Cell Biology, vol. 101, pp. 2023-2027 (Dec. 1985).
Rossi et al., "Effects of Repetitive Transcranial Magnetic Stimulation on Movement-related Cortical Activity in Humans," Cerebral Cortex, vol. 10, No. 8, pp. 802-808 (Aug. 2000).
Roux et al., "Chronic Motor Cortex Stimulation for Phantom Limb Pain: A Functional Magnetic Resonance Imagining Study: Technical Cast Report," Neurosurgery, vol. 48, No. 3, Mar. 2001, pp. 681-686.
Saitou et al., "Cerebral Blood Volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).
Sandkuhler, "Learning and memory in pain pathways," Pain 88, pp. 113-118 (2000).
Sanes, "The Relation between Human Brain Activity and Hand Movements," NeuroImage 11, pp. 370-374. (2000).
Sanes, J. and Donoghue, J.P., "Plasticity and Primary Motor Cortex," Annual Review of Neuroscience 23:393-415 (2000).
Schaefer, Pamela W. et al., "Assessing Tissue Viability with MR Diffusion and Perfusion Imaging," AJNR, 24: pp. 436-443 (Mar. 2003).
Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).
Schiff et al., "A neuromodulation strategy for rational therapy of complex brain injury states," Neurological Research, vol. 22 pp. 267-272 (Apr. 2000).
Schulz et al., "Localization of Epileptic Auras Induced on Stimulation by Subdural Electrodes," Epilepsia, Dec. 1997, vol. 38, Issue 12, pp. 1321-1329.
SCIRun, Scientific Computing and Imaging Institute. http://www.sofware.sci.utah.edu-scirun.html, 2 pages [Retrieved on Jul. 24, 2005].
Shimizu et al., "Therapeutic efficacy of transcranial magnetic stimulation for hereditary spinocerebellar degeneration," Tohoku Journal of Experimental Medicine, 189(3):203-11 (Nov. 1999).
Siebner et al., "Lasting cortical activation after repetitive TMS of the motor cortex," Neurology 54, pp. 956-963 (Feb. 2000).
Sioutos et al. Continuous Regional Cerebral Cortical Blood Flow Monitoring in Head-injured Patients, Neurosurgery, vol. 36, No. 5, May 1995, pp. 943-949.
Stefan et al., "Introduction of plasticity in the human motor cortex by paired associative stimulation," Brain, vol. 123, No. 3, pp. 572-584 (Mar. 2000).
Storer et al., "Microiontophoretic application of serotonin (5HT)1B/1D agonists inhibits trigeminal cell firing in the cat," Brain, 1997, vol. 120, Issue 12, pp. 2171-2177, Oxford University Press.
Strangman, Gary et al., "A Quantitative Comparison of Simultaneous Bold fMRI and NIRS Recordings during Functional Brain Activation," NeuroImage, vol. 17, pp. 719-731 (2002).
Strangman, Gary et al., "Factors affecting the accuracy of near-infrared spectroscopy concentration calculations for focal changes in oxygenation parameters," NeuroImage, vol. 18, pp. 865-879 (2003).
Strangman, Gary et al., "Non-Invasive Neuroimaging Using Near-Infrared Light," Biological Psychiatry, vol. 52, pp. 679-693 (2002).
Strens, Lucy et al., "The Ipsilateral Human Motor Cortex Can Functionally Compensate for Acute Contralateral Motor Cortex Dysfunction," Current Biology, vol. 13, pp. 1201-1205 (Jul. 15, 2003).
Suzuki et al., "Selective Electrical Stimulation of Postganglionic Cerebrovascular Parasympathetic Nerve Fibers Originating from the Sphenopalatine Ganglion Enhances Cortical Blood Flow in the Rat," Journal of Cerebral Blood Flow and Metabolism, May 1990, 10(3):383-91.
Taga, Gentaro et al., "Brain imaging in awake infants by near-infrared optical topogrpahy," PNAS, vol. 100, No. 19, pp. 10722-10727 (Sep. 16, 2003).
Tang, Cha-Min et al., "Optical Coherence Tomography of the Human Basal Ganglion," Deep Brain Stimulation Consortium Meeting Program Book, Sep. 29-30, 2003, Washington DC.
The GES 250 for Dense-Array EEG Research, Electrical Geodesics, Inc., http://www.egi.com/ges250r_n.html, 3 pages [Retrieved on Aug. 25, 2005].
The INVOS Cerebral Oximeter, Somanetics, http://www.somanetics.net/invos.htm, 1 page [retrieved from the internet on Dec. 22, 2005].
The National Institutes of Health (NIH) Consensus Development Program, "Surgery for Epilepsy," National Institutes of Health Consensus Development conference Statement, Mar. 19-21, 1990, 16 pages.
Theoret, Hugo et al., "Exploring Paradoxical Functional Facilitation with TMS," Supplements to Clinical Neurophysiology, vol. 56, pp. 211-219 (2003).
Thomas, Carmen et al., "Do Children with aggressive behavior have temporal lobe changes?" Alasbimn Journal, Year 5, No. 19, 8 pages (Jan. 2003).
Timmermann, Lars et al., "The cerebral oscillatory network of parkinsonian resting tremor," Brain, vol. 126, pp. 199-212, (2003).
Toronov, Vlad et al., "Near-infrared study of fluctuations in cerebral hemodynamics during rest and motor stimulation: Temporal analysis and spatial mapping," Medical Physics, vol. 27, No. 4, pp. 801-815 (Apr. 2000).
Tractography, Absolute Astronomy Reference, http://www.absoluteastronomy.com-encyclopedia-T-Tr-Tractography.htm, 2 pages [Retrieved on Jul. 24, 2005].
Tsubokawa, T. et al., "Chronic Motor Cortex Stimulation for the Treatment of Central Pain," Acta Neurochirurgica, Supplementum. vol. 52, pp. 137-139 (1991).
Tsubokawa, T. et al., "Chronic Motor Cortex Stimulation in Patients with Thalamic Pain," J. Neurosurg 78:393-401, (Mar. 1993).
Tsubokawa, T. et al., "Treatment of Thalamic Pain by Chronic Motor Cortex Stimulation", PACE, vol. 14, pp. 131-134 (Jan. 1991).
Tuch, D. et al., "Conductivity Tensor Mapping of the Human Brain Using Diffusion Tensor MRI," Neurobiology, vol. 98 No. 20, pp. 11697-11701 (Sep. 25, 2001).
Turton et al., "Contralateral and ipsilateral EMG responses to transcranial magnetic stimulation during recovery of arm and hand function after stroke," Electroencephalography and Clinical Neurophysiology 101 pp. 316-328 (1996).
Turton, A. and Lemon, R.N., "The contribution of fast corticospinal input to the voluntary activation of proximal muscles in normal subjects and in stroke patients," Exp. Brain Res., vol. 129, pp. 559-572 (1999).
Van Der Lee et al., "The Intra- and Interrater Reliability of the Action Research Arm Test: A Practical Test of Upper Extremity Function in Patients With Stroke," Arch. Phys. Med. Rehabil., vol. 82 pp. 14-19 (Jan. 2001).
Velasco et al. "Absolute and Relative Predictor Values of Some Non-Invasive and Invasive Studies for the Outcome of Anterior Temporal Lobectormy," Science Direct, vol. 31, Issue 1, Jan.-Feb. 2000, pp. 62-74, Elsevier Science, Inc.
Velasco et al., "Acute and Chronic Electrical Stimulation of the Centromedian Thalamic Nucleus: Modulation of Reticulo-Cortical Systems and Predictor Factors for Generalized Seizure Control," Archives of Medical Research, vol. 31, 2000, pp. 304-315, Elsevier Science, Inc.
Velasco et al., "Electrical Stimulation for Epilepsy: Stimulation of *Hippocampal Foci*," Stereotactic and Functional Neurosurgery, vol. 77, 2001, pp. 223-227.
Velasco et al., "Subacute and Chronic Electrical Stimulation of the Hippocampus on Intractable Temporal Lobe Seizures: Preliminary Report," Archives of Medical Research, vol. 31, 2000, pp. 316-328, Elsevier Science, Inc.
Velasco et al., "Subacute Electrical Stimulation of the Hippocampus Blocks Intractable Temporal Lobe Seizures and Paroxysmal EEG Activities," Epilepsia, vol. 41, No. 2, 2000, pp. 158-169, Lippincott Williams & Wilkins, Philadelphia.
Walker-Batson et al., "Amphetamine Paired With Physical Therapy Accelerates Motor Recovery After Stroke," Stroke, vol. 26, No. 12, pp. 2254-2259 (1995).

(56) References Cited

OTHER PUBLICATIONS

Waxman et al., "The Interictal Behavior Syndrome of Temporal Lobe Epilepsy," Arch Gen Psychiatry, vol. 32, Dec. 1975, pp. 1580-1586.
Weinand et al., "Cerebral blood flow and temporal lobe epileptogenicity," J Neurosurg, vol. 86, Feb. 1997, pp. 226-232.
Weinand et al., "Cerebral blood flow and temporal lobe epileptogenicity," Neurosurgical Focus, Nov. 1996, vol. 1, No. 5, aans.org, http://www.aans.org/education/journal/neurosurgical/nov96/1-5-3.asp, 17 pages.
Weinand et al., Long-term ictal monitoring with subdural strip electrodes: prognostic factors for selecting temporal lobectomy candidates, J Neurosurg, vol. 77, 1992, pp. 20-28.
Weinand et al., "Surface cortical cerebral blood flow monitoring and single photon emission computed tomography: prognostic factors for selecting temportal lobectormy candidates," Seizure, vol. 3, 1994, pp. 55-59.
Weinand et al., "Targeted Subthreshold Cortical Stimulation for Recovery of Motor Hand Function following Hemiparetic Stroke," Abstract: Apr. 18, 2005, AANS.org, http://www.aans.org/Library/Article.aspx?ArticleId=24934, 2 pages.
Weinand, Martin E. et al., "Cerebral blood flow and temporal lobe epileptogenicity," Retrieved from the Internet on Dec. 22, 2005, http://www.aans.org/education/journal/neurosurgical/nov96/1-5-3.asp, 13 pages.
Woodbury, D. et al., "Adult Rat and Human Bone Marrow Stromal Cells Differentiate Into Neurons," Journal of Neuroscience Research, 2000, vol. 61, pp. 364-370, Wiley Interscience, New York, NY.
Yamamoto et al., "Low-frequency Electric Cortical Stimulation Has an Inhibitory Effect on Epileptic Focus in Mesial Temporal Lobe Epilepsy," Epilepsia, vol. 43, No. 5, 2002, pp. 291-295, Blackwell Publishing, Inc.
Yokoh, Arika et al., "Intermittent versus continuous brain retraction," Journal of Neurosurgery, vol. 58, pp. 918-923 (Jun. 1983).
Ziemann et al., "Modulation of Plasticity in Human Motor Cortex after Forearm Ischemic Nerve Block," The Journal of Neuroscience 18(3):1115-1123 (Feb. 1998).
Sobotka, Stanisla et al. "Can Delay-Period Activity Explain Working Memory?" Journal of Neurophysiology, vol. 93, No. 1, Jan. 1, 2005.
International Search Report for Application No. PCT/US2008/060739; Applicant: Northstar Neuroscience, Inc.; Date of Mailing: Sep. 8, 2008 (6 pages).

\* cited by examiner

METHODS FOR ESTABLISHING PARAMETERS FOR NEURAL STIMULATION, INCLUDING VIA PERFORMANCE OF WORKING MEMORY TASKS, AND ASSOCIATED KITS

CROSS-REFERENCE TO RELATED APPLICATION

The present application is a continuation-in-part of pending U.S. application Ser. No. 11/254,240 filed Oct. 19, 2005 and incorporated herein in its entirety by reference.

TECHNICAL FIELD

The present disclosure in directed generally toward methods and systems for establishing parameters for neural stimulation, including, but not limited to, techniques for determining signal delivery parameters for treating patient depression, based at least in part on the patient's performance of a working memory task.

BACKGROUND

A wide variety of mental and physical processes are controlled or influenced by neural activity in particular regions of the brain. In some areas of the brain, such as in the sensory or motor cortices, the organization of the brain resembles a map of the human body; this is referred to as the "somatotopic organization of the brain." There are several other areas of the brain that appear to have distinct functions that are located in specific regions of the brain in most individuals. For example, areas of the occipital lobes relate to vision, regions of the left inferior frontal lobes relate to language in the majority of people, and regions of the cerebral cortex appear to be consistently involved with conscious awareness, memory, and intellect. This type of location-specific functional organization of the brain, in which discrete locations of the brain are statistically likely to control particular mental or physical functions in normal individuals, is herein referred to as the "functional organization of the brain."

Many problems or abnormalities with body functions can be caused by damage, disease and/or disorders of the brain. A stroke, for example, is one very common condition that damages the brain. Strokes are generally caused by emboli (e.g., obstruction of a vessel), hemorrhages (e.g., rupture of a vessel), or thrombi (e.g., clotting) in the vascular system of a specific region of the cortex, which in turn generally causes a loss or impairment of a neural function (e.g., neural functions related to face muscles, limbs, speech, etc.). Stroke patients are typically treated using physical therapy to rehabilitate the loss of function of a limb or another affected body part. For most patients, little can be done to improve the function of the affected limb beyond the recovery that occurs naturally without intervention.

One existing physical therapy technique for treating stroke patients constrains or restrains the use of a working body part of the patient to force the patient to use the affected body part. For example, the loss of use of a limb is treated by restraining the other limb. Although this type of physical therapy has shown some experimental efficacy, it is expensive, time-consuming and little-used. Stroke patients can also be treated using physical therapy plus adjunctive therapies. For example, some types of drugs, including amphetamines, increase the activation of neurons in general. These drugs also appear to enhance neural networks. However, these drugs may have limited efficacy because the mechanisms by which they operate are very non-selective and they cannot be delivered in high concentrations directly at the site where they are needed. Still another approach is to apply electrical stimulation to the brain to promote the recovery of functionality lost as a result of a stroke. While this approach has been generally effective, it has not adequately addressed all stroke symptoms.

In addition to the motor-related symptoms described above, stroke patients may also suffer from cognitive defects. For example, patients may suffer from neglect, a defect that causes patients to lose cognizance of portions of their surroundings and/or themselves. In other cases, patients may suffer from other cognitive defects, such as memory loss or loss of reasoning ability, in connection with a stroke or other event that causes neural damage. While electromagnetic stimulation has been proposed generally to address cognitive defects, the application of such techniques may in some cases be difficult because, unlike motor neurons, which can immediately indicate activation by a corresponding muscle action, cognitive and other non-motor neurons typically do not provide such a readily discernable indication of activation. Accordingly, there is a need to improve the manner in which stimulation is applied to cognitive and other non-motor neurons.

DETAILED DESCRIPTION

A. Introduction

The present disclosure is directed generally toward methods and systems for establishing stimulation parameters for neural stimulation processes and using the established parameters to treat a patient's neural dysfunction. In particular embodiments, the methods and systems are directed to establishing stimulation parameters for non-motor and/or non-sensory neurons. In still further embodiments, the stimulation parameters selected for stimulating a target neural population can be based at least in part on performance of a function controlled at least in part by the target neural population.

Figure 1A:
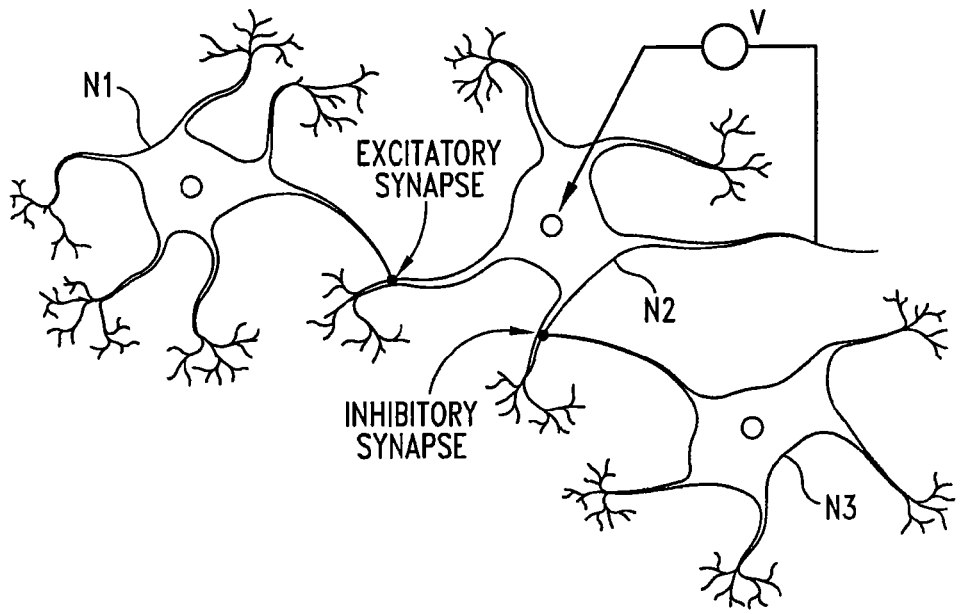
FIG. 1A is a schematic view of neurons.
Figure 1B:
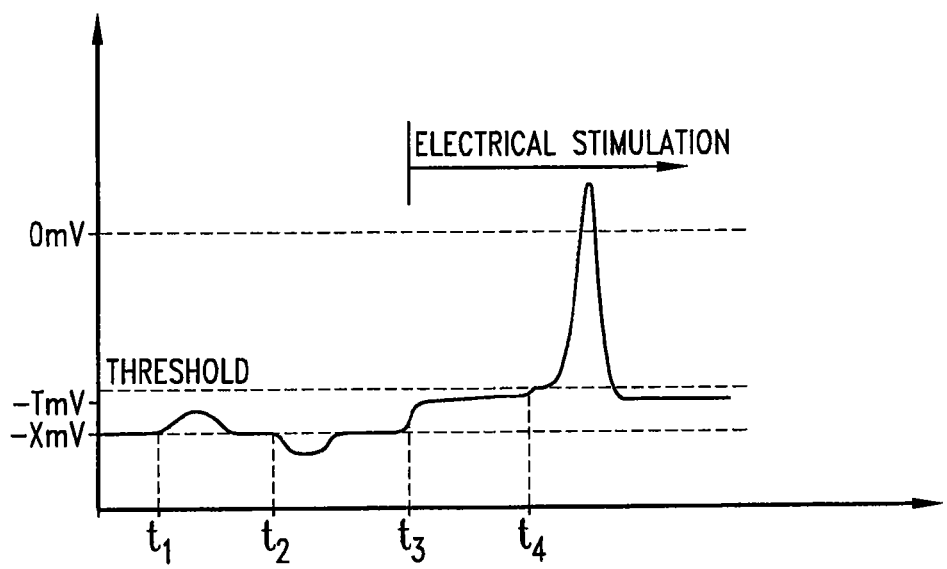
FIG. 1B is a graph illustrating firing an "action potential" associated with normal neural activity.

FIG. 1A is a schematic representation of several neurons N1-N3 and FIG. 1B is a graph illustrating an "action potential" related to neural activity in a normal neuron. Neural activity is governed by electrical impulses generated in neurons. For example, neuron N1 can send excitatory inputs to neuron N2 (e.g., at time $t_1$ in FIG. 1B), and neuron N3 can send inhibitory inputs to neuron N2 (e.g., at time $t_2$ in FIG. 1B). The neurons receive/send excitatory and inhibitory inputs from/to a population of other neurons. The excitatory and inhibitory inputs can produce "action potentials" in the neurons, which are electrical pulses that travel through neurons by changing the flux of sodium (Na) and potassium (K) ions across the cell membrane. An action potential occurs when the resting membrane potential of the neuron surpasses a threshold level. When this threshold level is reached, an "all-or-nothing" action potential is generated. The action potentials propagate down the length of the axon (the long portion of the neuron that makes up nerves or neuronal tracts) to cause the release of neurotransmitters from that neuron that will further influence adjacent neurons, as described further below.

At times $t_1$ and $t_2$, the depolarization waves generated in response to the intrinsic excitatory/inhibitory inputs from other neurons do not summate in a manner that "bridges-the-gap" from a neural resting potential at $-X$ mV (e.g., approximately $-70$ mV) to a threshold firing potential at $-T$ mV (e.g., approximately $-50$ mV). At time $t_3$, extrinsic electrical stimulation is applied to the brain, in this case at an intensity or level that is expected to augment or increase the magnitude of descending depolarization waves generated by the dendrites, yet below an intensity or level that by itself will be sufficient to summate in a manner that induces action potentials and triggers the neural function corresponding to these neurons. Extrinsic stimulation signals applied in this manner may generally be referred to as subthreshold signals. At time $t_4$, the neurons receive another excitatory input. In association with a set of appropriately applied extrinsic stimulation signals, even a small additional intrinsic input may result in an increased likelihood that a summation of the descending depolarization waves generated by the dendrites will be sufficient to exceed the difference between the neural resting potential and the threshold firing potential to induce action potentials in these neurons. Thus, in this situation, the subthreshold extrinsic signals facilitate the generation of action potentials in response to intrinsically occurring neural signaling processes. It is to be understood that depending upon signal parameters, the extrinsic signals may exert an opposite (disfacilitatory, inhibitory, or disruptive) effect upon neurons or neural signaling processes, and hence particular signal parameters may be selected in accordance with a likelihood of achieving a desired or intended therapeutic effect or outcome at any given time.

In many instances, it may be desirable to electrically stimulate neurons at subthreshold levels. For example, it may be desirable to provide stimulation to motor neurons at subthreshold levels, and then rely on the (perhaps limited) ability of the neuron to supplement the stimulation signal. The combination of the external electrical stimulation and the neuron's internal or intrinsic ability to generate at least some increase in potential can be enough to exceed the threshold level and generate an action potential. In such instances, it can be important to determine, approximately determine, or estimate what the threshold potential for a given neural population is. Otherwise, the target neurons may be overstimulated, or the neurons may not receive a therapeutically useful dose of stimulation (e.g., if the stimulation is provided outside of a particular stimulation parameter range). In particular instances, however, it may be desirable to briefly stimulate neurons with near threshold, threshold, and/or suprathreshold pulses or bursts, possibly in association with subthreshold stimulation.

In the case of motor neurons, a threshold level can generally be readily determined by varying a stimulation parameter (e.g., increasing a voltage, current, and/or frequency of the stimulation signal) until a motor response is detected. The motor response can often be detected by simply observing or measuring (e.g., using electromyography (EMG)) a muscle action exhibited by the patient. In a generally similar manner, particular sensory neurons can be stimulated and a threshold for such neurons can be detected when the patient receives, reports, or becomes aware of a corresponding sensation. However, for at least some neurons, it may be difficult to detect when the threshold level is exceeded because the patient neither displays an outward action nor reports a sensation. This difficulty can arise, for example, when stimulating neurons associated with cognitive function; or more generally, when stimulating neurons that may be associated with patient functions or responses that are difficult and/or time consuming to readily observe or measure. Such neurons are referred to herein as "silent" neurons.

A method for treating a patient in accordance with one aspect includes engaging the patient in a function (e.g., a cognitive function) controlled at least in part by a target neural population, and applying electromagnetic signals to the target neural population. The method can further include adjusting a target parameter in accordance with which the electromagnetic signals are applied to the patient, based at least in part on a characteristic of the patient's performance of the function. The method can still further include applying the electromagnetic signals to the patient with the adjusted target parameter and evaluating the patient's response to the electromagnetic signals, including the characteristic of the patient's performance. Based at least in part on the evaluation of the patient's response, the method can further include determining whether to apply further electromagnetic signals to the patient, establishing a value of the target parameter for applying further electromagnetic signals to the patient, and/or adjusting another target parameter in accordance with which the electromagnetic signals are applied to the patient.

A method for treating a patient in accordance with another aspect includes applying electromagnetic test signals to a target neural population at the frontal lobe of the patient, and adjusting a current with which the signals are delivered, while engaging the patient in a cognitive function. The method can further include ceasing to apply the test signals if the patient's performance of the cognitive function falls below a threshold level, or if the patient exhibits seizure behavior. The method can then further include determining a current limit based at least in part on a value of the current when the patient's performance of the cognitive function falls below the threshold level, and applying electromagnetic therapy signals to the patient at a current level that is at or below the current limit.

Still a further aspect is directed to a kit for treating a non-motor, non-sensory neurological dysfunction in a patient. The kit can include an electrode device having at least one electrode positioned to be implanted beneath a patient's skull, and a lead coupled to the electrode device and coupleable to a signal generator having an adjustable output. The kit can still further include a volitional neurological test administrable to the patient. For example, the test can include a memory test, a verbal performance test, and/or a mathematical test.

Figure 1C:
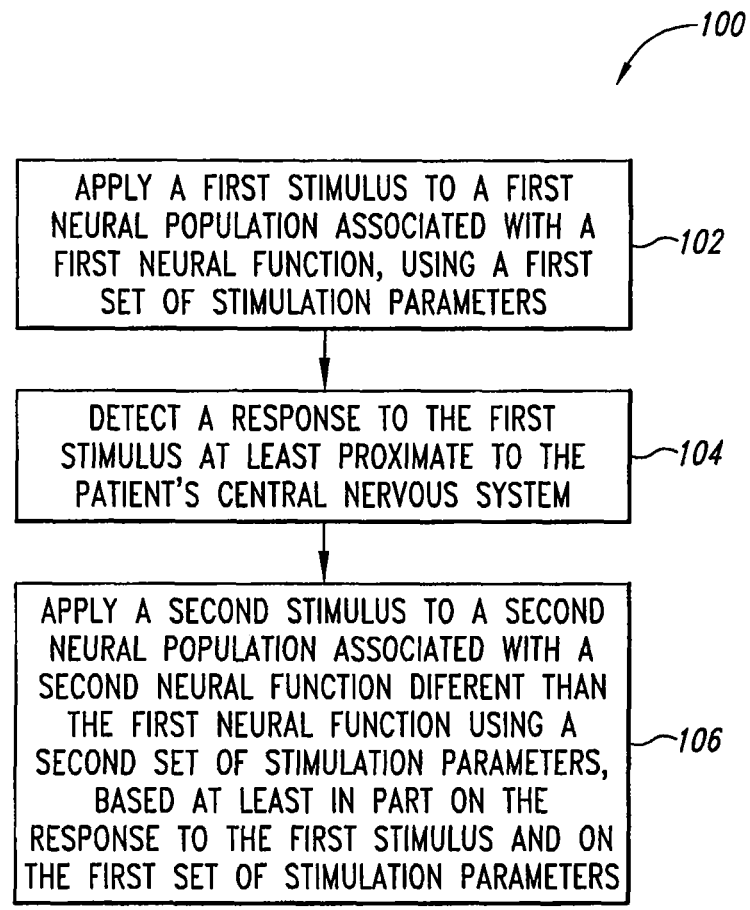
FIG. 1C is a flow chart illustrating a method for applying stimuli to different neural populations in accordance with an embodiment of the invention.

B. Methods for Establishing Stimulation Parameters, Including Stimulation Parameters for Diverse Neural Populations FIG. 1C is a flow diagram illustrating a process 100 for treating a patient in accordance with an embodiment of the invention. The process 100 can include applying a first stimulus to a first neural population associated with a first neural function, using a first set of stimulation parameters (process portion 102). As used in this context, "associated" refers generally to neurons whose activity correlates with a particular neural function. Accordingly, such neurons can be (but need not be) directly or indirectly responsible for executing the function. For example, process portion 102 can include applying an electrical stimulation to a motor neuron using a selected current, voltage, and waveform. In process portion 104, the method can include detecting a response to the first stimulus at least proximate to the patient's central nervous system. For example, process portion 104 can include detecting a change in electrical signals generated by the first neural population, or a change in hemodynamic properties of the blood proximate to the first neural population. Hemodynamic properties can include blood flow levels or blood volume proximate to the first neural population, or a change in a chemical species level (e.g., corresponding to an oxygenation level) of the blood.

Process portion 106 can include applying a second stimulus to a second neural population associated with a second neural function different than the first neural function. For example, process portion 106 can include applying a second stimulus to a cognitive, neuropsychological, neuropsychiatric, or other "silent" neuron. The second stimulus can be applied using a second set of stimulation parameters, the selection of which is based at least in part on the response to the first stimulus and on the first set of stimulation parameters. For example, if the first set of stimulation parameters have a desired relationship relative to the threshold level of the first neural population, then the second set of stimulation parameters can be selected based at least in part on the first stimulation parameters, so as to produce a similar (or calculatedly different) relationship relative to an expected threshold level for the second neural population. In a particular embodiment, a practitioner can determine one or more parameters corresponding to the threshold level of stimulation for a motor neuron, and can interpolate or extrapolate these data to provide a corresponding threshold or non-threshold level of stimulation for a non-motor neuron. In a further particular embodiment, the practitioner can select values for one or more parameters in a manner expected to provide stimulation at between 10% and 90% (e.g., between approximately 25% and 75%, or at approximately 50%) of the threshold value for the non-motor neuron, based on data obtained from stimulation of a motor neuron. If the threshold level is expected to change (e.g., drift) during the course of treatment, the practitioner can update the stimulation parameters accordingly. This function can also be performed automatically in some embodiments.

In another embodiment, if it is determined that stimulating the first neural population with the first set of stimulation parameters produces a desired or beneficial result, some or all aspects of the second set of stimulation parameters (applied to the second neural population) can be selected to be at least approximately identical to the first set of stimulation parameters. A beneficial result in the case of a motor neural population may be the patient's increased ability to perform a motor task. When the same or a similar stimulation parameter is used to stimulate a cognitive neural population, the beneficial result may be the patient's increased ability to perform a cognitive task.

Figure 2:
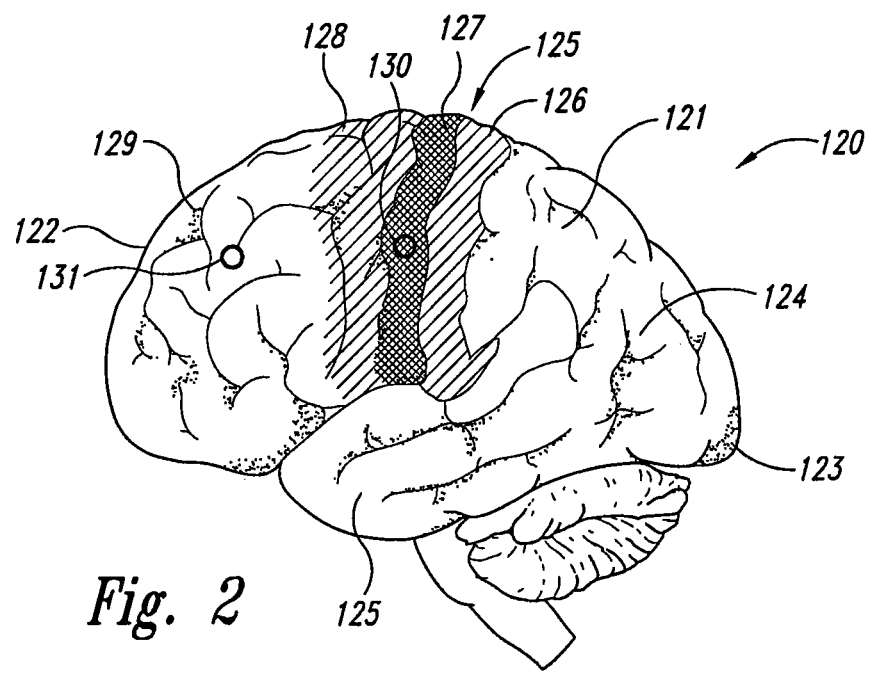
FIG. 2 is a side elevation view of a human brain illustrating prominent brain structures and representative stimulation sites in accordance with an embodiment of the invention.

FIG. 2 is a partially schematic illustration of the left side of a human brain 120 illustrating the four major brain lobes, e.g., the parietal lobe 121, the frontal lobe 122, the occipital lobe 124 (which includes the visual cortex 123), and the temporal lobe 125. The parietal lobe 121 and the frontal lobe 122 are separated by the central sulcus 125, with the precentral gyrus (or primary motor cortex) 127 located anterior to the central sulcus, and the postcentral gyrus (or primary somatosensory cortex) 126 located posterior to the central sulcus. Stimulation provided at the primary motor cortex 127 can produce a motor response, and stimulation provided at the primary somatosensory cortex 126 can provide a sensory response in the patient. Also shown are the premotor cortex 128, positioned anterior to the primary motor cortex 127, and the prefrontal cortex 129, positioned anterior to the premotor cortex.

Figure 8:
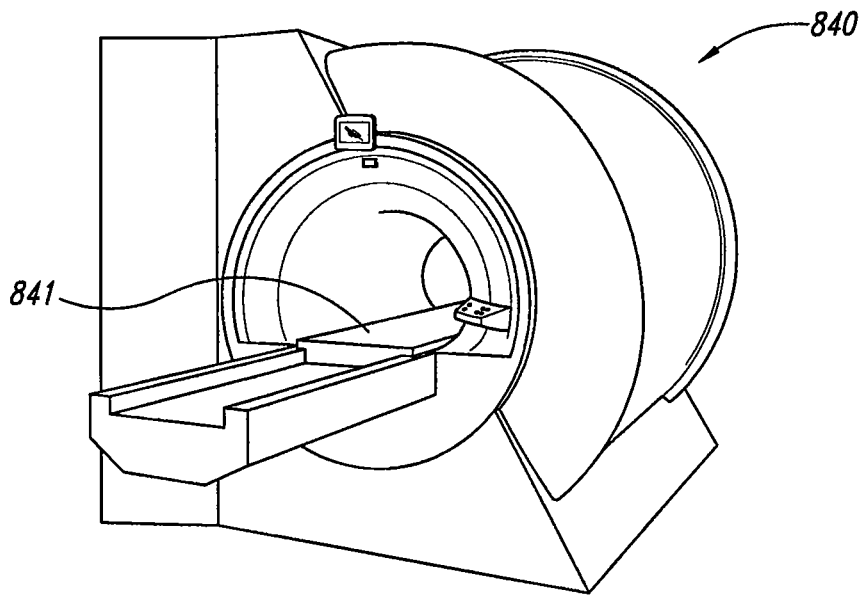
FIG. 8 is a partially schematic, isometric illustration of a magnet resonance chamber in which the effects of neural stimulation may be evaluated.
Figure 9:
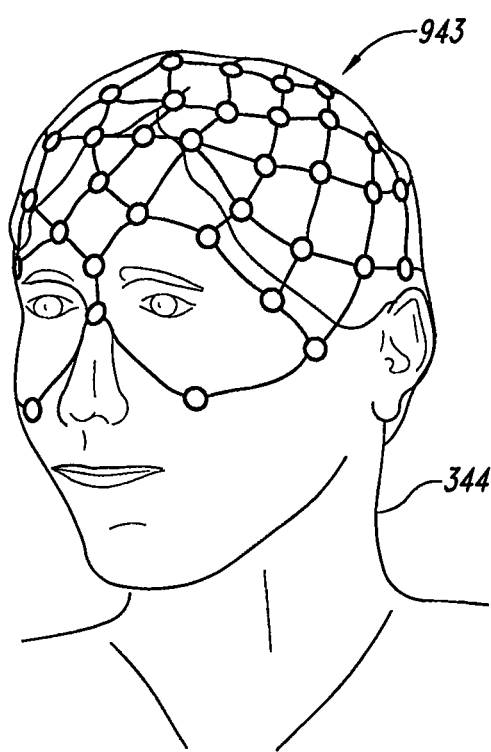
FIG. 9 illustrates a patient wearing a network of electrodes positioned to detect brain activity in accordance with further embodiments of the invention.

In some instances, it may be desirable to stimulate the prefrontal cortex 129, for example, to provide a cognitive or neuropsychological, neuropsychiatric, and/or other benefit to the patient. However, as described above, it may not be immediately apparent what stimulation parameters should be used to produce the desired beneficial effect because (a) the patient may not exhibit a readily ascertainable external response indicating when the threshold level is closely approached, reached, or exceeded, and/or (b) it may require a significant period of time to determine whether the stimulation produces long-lasting cognitive benefits to the patient. Accordingly, a practitioner can first provide stimulation to a first neural population 130 located at the primary motor cortex 127 to identify stimulation parameters that can then be applied to a second neural population 131 located at the prefrontal cortex 129. FIGS. 3-7 (described below) illustrate devices that can be used to apply the stimulus to the first neural population and/or the second neural population 131. FIGS. 8 and 9 (also described below) illustrate devices that can be used to detect responses to the stimuli provided by these devices.

C. Applying Electrical Stimulation

Figure 3:
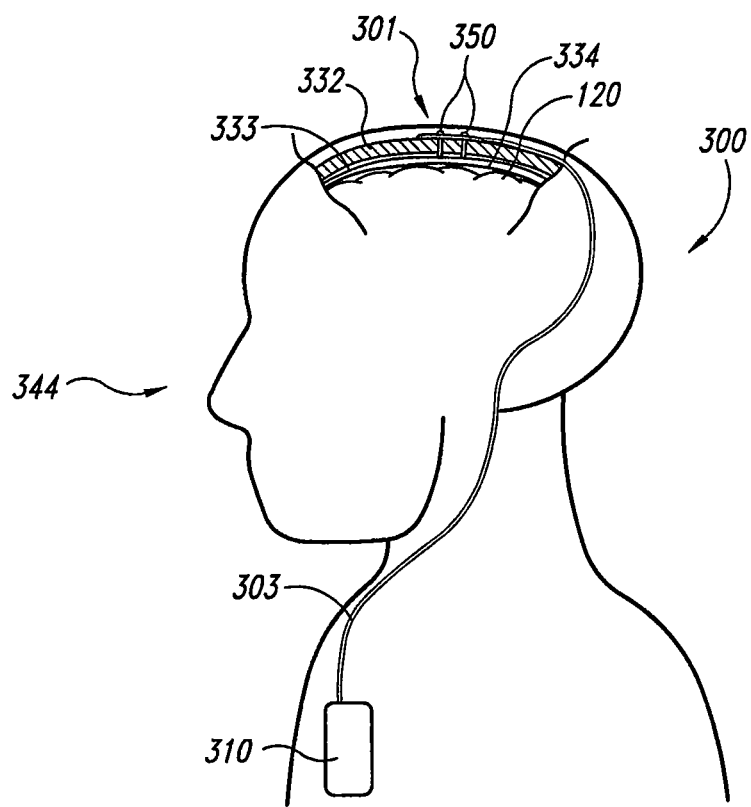
FIG. 3 is a partially schematic illustration of a stimulation device configured in accordance with an embodiment of the invention.

FIGS. 3-7 illustrate representative devices for applying electrical stimulation. These devices can be located at a first stimulation site to provide stimulation to the first neural population 130 (described above with reference to FIG. 2) using the first set of stimulation parameters. Once the second set of stimulation parameters is determined (based on results from stimulating the first neural population 130), the same or similar devices located at a second stimulation site can provide stimulation to the second neural population 131 (FIG. 2). FIG. 3 is a schematic illustration of a neurostimulation system 300 implanted in the patient 344 to provide stimulation in accordance with several embodiments of the invention. The system 300 can include an electrode device 301 carrying one or more electrodes 350. The electrode device 301 can be positioned in the skull 332 of the patient 344, with the electrodes 350 positioned to stimulate target areas of the brain 120. For example, the electrodes 350 can be positioned just outside the dura mater 333 (which surrounds the brain 120) to stimulate cortical tissue. In another embodiment described later with reference to FIG. 7, an electrode can penetrate the dura mater 333 to stimulate subcortical tissues. In still further embodiments, the electrodes 350 can penetrate the dura mater 333 but not the underlying pia mater 334, and can accordingly provide stimulation signals through the pia mater 334.

The electrode device 301 can be coupled to a pulse system 310 with a communication link 303. The communication link 303 can include one or more leads, depending (for example) upon the number of electrodes 350 carried by the electrode device 301. The pulse system 310 can direct electrical signals to the electrode device 301 to stimulate target neural tissues.

Figure 4:
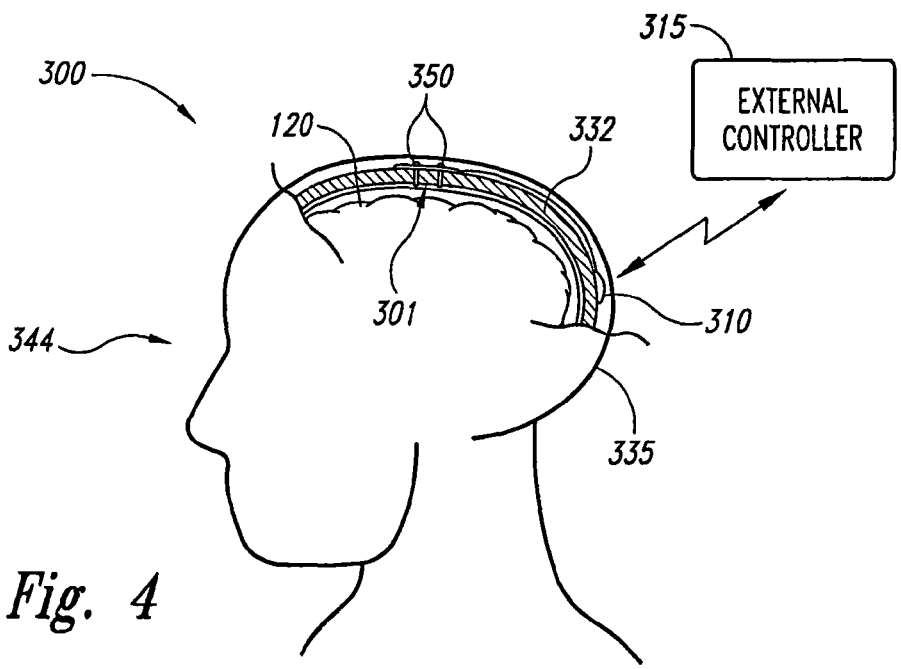
FIG. 4 illustrates a stimulation device operatively coupled to an external controller in accordance with another embodiment of the invention.

The pulse system 310 can be implanted at a subclavicular location, as shown in FIG. 3. In particular embodiments, the pulse system 310 (and/or other implanted components of the system 300) can include titanium and/or other materials that can be exposed to magnetic fields generated by magnetic resonance chambers without harming the patient. The pulse system 310 can also be controlled internally via pre-programmed instructions that allow the pulse system 310 to operate autonomously after implantation. In other embodiments, the pulse system 310 can be implanted at other locations, and at least some aspects of the pulse system 310 can be controlled externally. For example, FIG. 4 illustrates an embodiment of the system 300 in which the pulse system 310 is positioned on the external surface of the skull 332, beneath the scalp 335. The pulse system 310 can be controlled internally and/or via an external controller 315.

Figure 5:
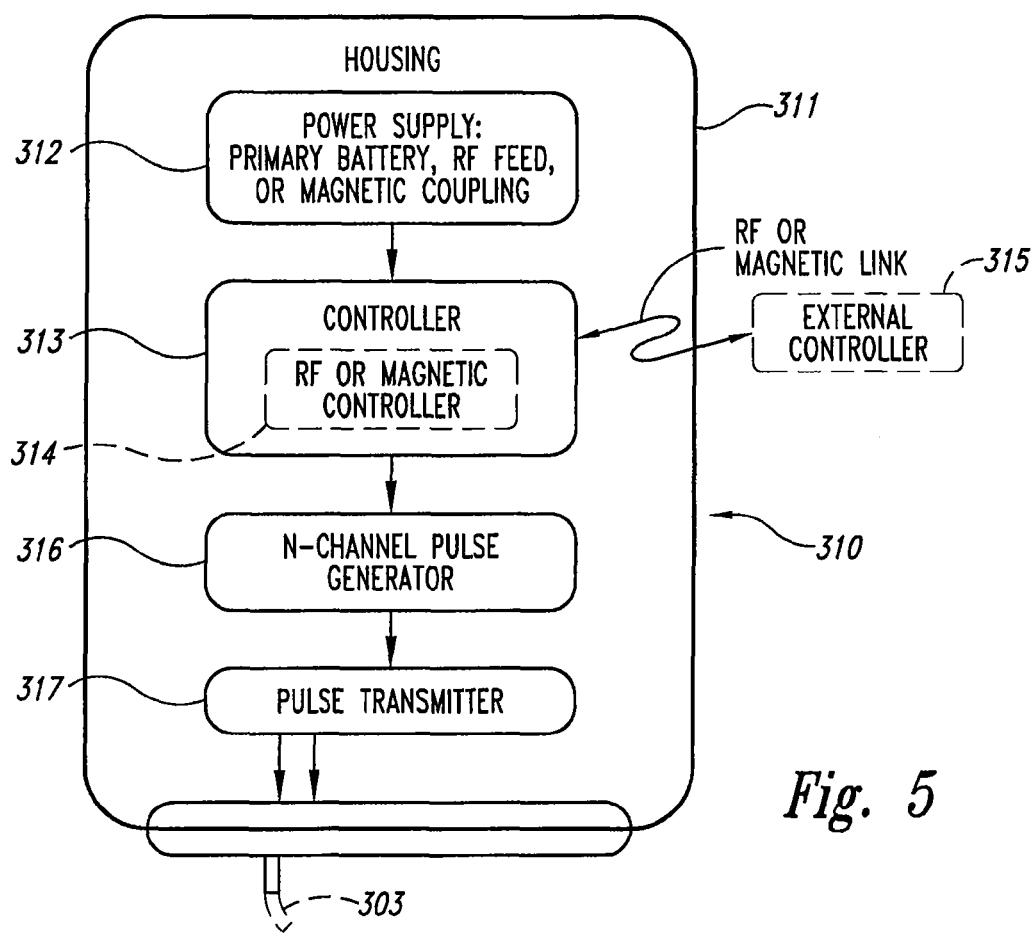
FIG. 5 is a schematic illustration of a pulse system configured in accordance with an embodiment of the invention.

FIG. 5 schematically illustrates a representative example of a pulse system 310 suitable for use in the neural stimulation system 300 described above. The pulse system 310 generally includes a housing 311 carrying a power supply 312, an integrated controller 313, a pulse generator 316, and a pulse transmitter 313. The power supply 312 can be a primary battery, such as a rechargeable battery or other suitable device for storing electrical energy. In other embodiments, the power supply 312 can be an RF transducer or a magnetic transducer that receives broadcast energy emitted from an external power source and that converts the broadcast energy into power for the electrical components of the pulse system 310.

In one embodiment, the integrated controller 313 can include a processor, a memory, and a programmable computer medium. The integrated controller 313, for example, can be a microcomputer, and the programmable computer medium can include software loaded into the memory of the computer, and/or hardware that performs the requisite control functions. In another embodiment identified by dashed lines in FIG. 5, the integrated controller 313 can include an integrated RF or magnetic controller 314 that communicates with the external controller 315 via an RF or magnetic link. In such an embodiment, many of the functions performed by the integrated controller 313 may be resident on the external controller 315 and the integrated portion 314 of the integrated controller 313 may include a wireless communication system.

The integrated controller 313 is operatively coupled to, and provides control signals to, the pulse generator 316, which may include a plurality of channels that send appropriate electrical pulses to the pulse transmitter 317. The pulse generator 316 may have multiple channels, with at least one channel associated with a particular one of the electrodes 350 described above. The pulse generator 316 sends appropriate electrical pulses to the pulse transmitter 317, which is coupled to the electrodes 350 (FIG. 1). In one embodiment, each of these electrodes 350 is configured to be physically connected to a separate lead, allowing each electrode 350 to communicate with the pulse generator 316 via a dedicated channel. Suitable components for the power supply 312, the integrated controller 313, the external controller 315, the pulse generator 316, and the pulse transmitter 317 are known to persons skilled in the art of implantable medical devices.

The pulse system 310 can be programmed and operated to adjust a wide variety of stimulation parameters, for example, which electrodes are active and inactive, whether electrical stimulation is provided in a unipolar or bipolar manner, and/or how the stimulation signals are varied. In particular embodiments, the pulse system 310 can be used to control the polarity, frequency, duty cycle, amplitude, and/or spatial and/or temporal qualities of the stimulation. The stimulation can be varied to match naturally occurring burst patterns (e.g., theta burst stimulation), and/or the stimulation can be varied in a predetermined, pseudorandom, and/or aperiodic manner at one or more times and/or locations.

Figure 6:
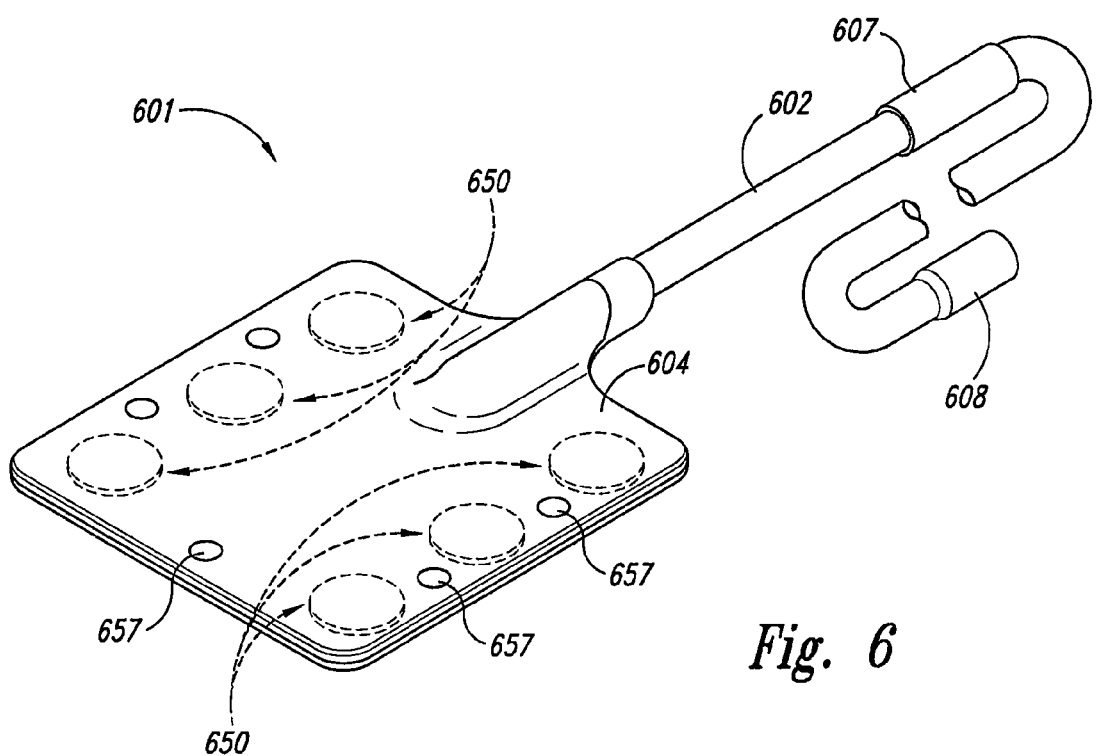
FIG. 6 is an isometric illustration of a device that carries electrodes in accordance with another embodiment of the invention.

Stimulation can be provided to the patient using devices in addition to or in lieu of those described above. For example, FIG. 6 is a top, partially hidden isometric view of an embodiment of an electrode device 601 configured to carry multiple cortical electrodes 650. The electrodes 650 can be carried by a flexible support member 604 (located within the patient's skull) to place each electrode 650 at a stimulation site of the patient when the support member 604 is implanted within the patient's skull. Electrical signals can be transmitted to the electrodes 650 via leads carried in a communication link 603. The communication link 603 can include a cable 602 that is connected to the pulse system 310 (FIG. 3) via a connector 608, and is protected with a protective sleeve 607. Coupling apertures or holes 657 can facilitate temporary attachment of the electrode device 601 to the dura mater at, or at least proximate to, a stimulation site. The electrodes 650 can be biased cathodally and/or anodally, as described above. In an embodiment shown in FIG. 6, the electrode device 601 can include six electrodes 650 arranged in a 2×3 electrode array (i.e., two rows of three electrodes each), and in other embodiments, the electrode device 601 can include more or fewer electrodes 650 arranged in symmetrical or asymmetrical arrays. The particular arrangement of electrodes 650 can be selected based on the region of the patient's brain that is to be stimulated, and/or the patient's condition.

In a particular embodiment, a device generally similar to the device shown in FIG. 6 can be constructed and positioned to extend over both the first neural population 130 (FIG. 2)

and the second neural population 131 (FIG. 2). Accordingly, the practitioner can implant a single device that allows the practitioner to stimulate motor neurons (or another neural population used to determine stimulation parameters) and provide stimulation to a population of silent neurons (e.g., cognitive neurons or other silent neurons). The stimulation of motor neurons and silent neurons may occur simultaneously, sequentially, or separately. The electrode device may include a two-dimensional array of electrodes as shown in FIG. 6, or can include a linear arrangement or other arrangement of electrodes, depending upon the particular neural populations to be stimulated.

Figure 7:
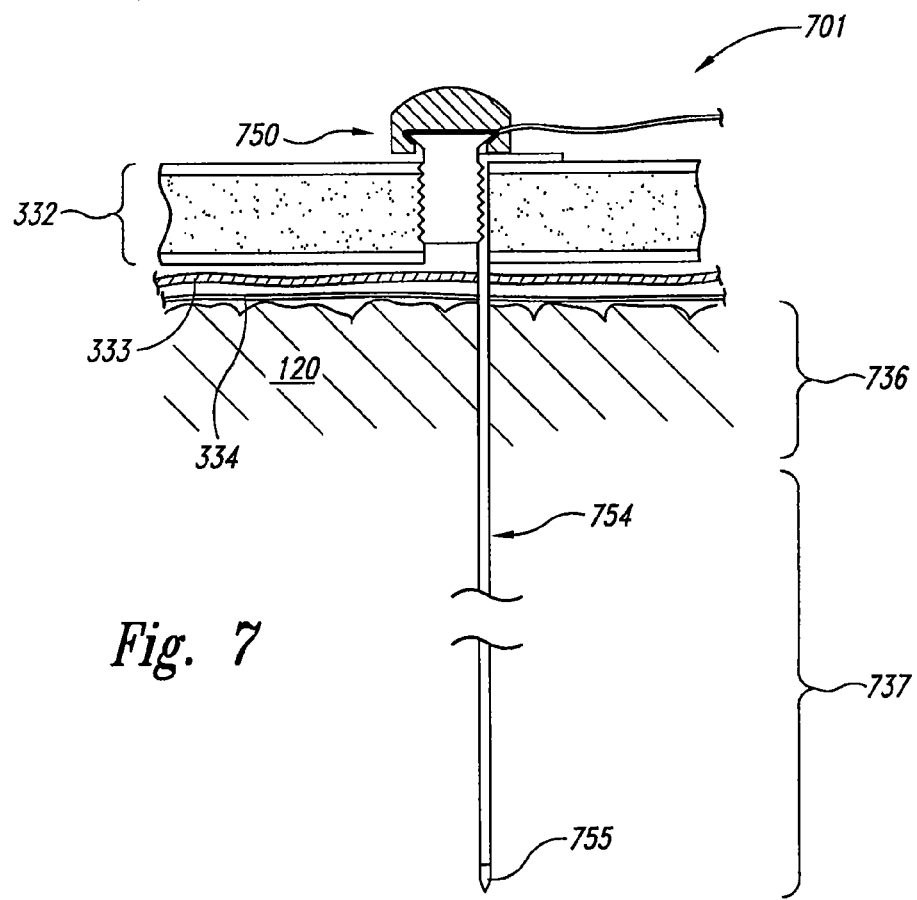
FIG. 7 is a partially schematic, side elevation view of an electrode configured to deliver electromagnetic stimulation to a subcortical region in accordance with an embodiment of the invention.

FIG. 7 illustrates an electrode device 701 that may be configured to apply electrical stimulation signals to a cortical region 736 or a subcortical region 737 of the brain 120 in accordance with further embodiments of the invention. The electrode device 701 can include an electrode 750 having a head and a threaded shaft that extends through a pilot hole in the patient's skull 332. If the electrode 750 is intended for cortical stimulation, it can extend through the skull 332 to contact the dura mater 333 or the pia mater 334. If the electrode 750 is to be used for subcortical stimulation, it can include an elongate conductive member 754 that extends downwardly through the cortical region 736 into the subcortical region 737. Most of the length of the elongate conductive member 754 can be insulated, with just a tip 755 exposed to provide electrical stimulation in only the subcortical region 737. Subcortical stimulation may be appropriate in at least in some instances, for example, when the brain structures such as the basal ganglia are to be stimulated. In other embodiments, other deep brain structures (e.g., the amygdala or the hippocampus) can be stimulated using a subcortical electrode. If the hippocampus is to be stimulated, stimulation may be provided to the perihippocampal cortex using a subdurally implanted electrode that need not penetrate through brain structures other than the dura.

Further details of electrode devices that may be suitable for electromagnetic stimulation in accordance with other embodiments of the invention are described in the following pending U.S. Patent Applications, all of which are incorporated herein by reference: Ser. No. 10/891,834, filed Jul. 15, 2004; Ser. No. 10/418,796, filed Apr. 18, 2003; and Ser. No. 09/802,898, filed Mar. 8, 2001. Further devices and related methods are described in a copending U.S. application Ser. No. 11/255,187, titled "Systems and Methods for Patient Interactive Neural Stimulation and/or Chemical Substance Delivery," and U.S. application Ser. No. 11/254,060, titled "Methods and Systems for Improving Neural Functioning, Including Cognitive Functioning and Neglect Disorders," both incorporated herein by reference.

In still further embodiments, other techniques may be used to provide stimulation to the patient's brain. Such techniques can include electromagnetic techniques in addition to purely electrical techniques. In particular, such techniques can include transcranial magnetic stimulation techniques, which do not require that an electrode be implanted beneath the patient's skull. In still further embodiments, other techniques, which also may not require an implant, can be used. Such additional techniques can include transcranial direct current stimulation.

D. Techniques For Detecting a Response to Neural Stimulation

Once the appropriate stimulation device has been selected and positioned, the practitioner can apply stimulation and, particularly if the practitioner is stimulating the first neural population, detect a response. The practitioner may also wish to detect a response when stimulation is applied to the second neural population, e.g., to verify that the stimulation provided in accordance with the second set of stimulation parameters is or appears to be producing a desired response, condition, state, or change. In a particular aspect of either process, the response is detected at least proximate to the patient's central nervous system, and in a further particular aspect, at the patient's brain. One or more of several techniques may be employed to determine the neural response to the stimulation. Many suitable techniques rely on hemodynamic properties, e.g., they measure or are based on concentrations of oxy-hemoglobin and/or deoxy-hemoglobin. Such techniques can include functional magnetic resonance imaging (fMRI), measurements or estimates of cerebral blood flow, cerebral blood volume, cerebral metabolic rate of oxygen (CMRO), Doppler flowmetry, and/or optical spectroscopy using near infrared radiation. Magnetic resonance techniques (e.g., fMRI techniques) can be performed inside a magnetic resonance chamber, as described below with reference to FIG. 8.

Certain other techniques, e.g., thermal measurements and/or flowmetry techniques, can be performed subdermally on the patient. Still further techniques, in particular, optical techniques such as near infrared spectroscopy techniques, are generally noninvasive and do not require penetration of the patience's scalp or skull. These techniques can include placing a near infrared emitter and detector (or an array of emitter/detector pairs) on the patient's scalp to determine species concentrations of both oxy-hemoglobin and deoxy-hemoglobin. Representative devices for measuring hemodynamic quantities (that correspond to neural activity) are disclosed in U.S. Pat. No. 5,024,226, U.S. Pat. No. 6,615,065, both incorporated herein by reference, and are available from ISS, Inc. of Champaign, Ill., and Somanetics of Troy, Mich. Further devices and associated methods are disclosed in pending U.S. application Ser. No. 11/583,349 titled "Neural Stimulation and Optical Monitoring Systems and Methods," incorporated herein by reference. Any of the foregoing techniques can be used to identify and/or quantify parameters and/or states associated with the patient's level of neural functioning. Such states may determine, influence, and/or alter signal properties such as intensity, power, spectral, phase, coherence, and/or other signal characteristics.

FIG. 8 illustrates a magnetic resonance imaging system 840 having a patient platform 841 for carrying the patient during a procedure for detecting responses to stimulation. Functional MRI techniques can be used to correlate levels of brain activity with stimulation provided to the patient's brain via one or more stimulation parameters. If the stimulation is to be provided via implanted devices, the implanted devices are selected to be compatible with the strong magnetic fields generated by the chamber.

Some embodiments of the invention may involve magnetic resonance spectroscopy (MRS) techniques, which may facilitate the identification or determination of various chemical species and/or relative concentration relationships between such species in particular brain regions. Stimulation sites may be selected based upon, for example, a detected imbalance between particular neurotransmitters. Additionally or alternatively, the effect(s) of neural stimulation may be evaluated or monitored on a generally immediate, short term, and/or long term basis using MRS and/or other imaging techniques.

FIG. 9 illustrates a patient wearing an electrode net 943 that includes a network of receptor electrodes positioned over the patient's scalp to sense, detect, or measure electroencephalographic (EEG) signals corresponding to the patient's neuroelectric activity. In a representative embodiment, the electrode net 943 may include a Geodesic Sensor Net manufactured by Electrical Geodesics, Inc., of Eugene, Oreg. When external or non-intrinsic electromagnetic stimulation generates or affects a locational, spectral, and/or temporal response or change in the patient's neuroelectric activity, such responses or changes in the patient's neuroelectric signals can be sensed or detected by the electrode net 943. Accordingly, the detected properties of or changes in neuroelectric signals (or the relative absence of particular characteristics or changes) can be used to determine whether the threshold level for a target neural population has been met. In particular embodiments, the foregoing sensors can provide coherence information, which relates to the rhythmic or synchronous aspects of the patient's neural activity. Further details regarding coherence are disclosed in co-pending U.S. application Ser. No. 10/782,526, filed on Feb. 19, 2004 and incorporated herein by reference.

In other embodiments, a net (or other network) generally similar to that shown in FIG. 9 can be outfitted with sensors other than electrical sensors. For example, such a net can be outfitted with near infrared sensors or other optical sensors. Such sensors may detect changes in neural activity arising in association with subthreshold, threshold, and/or suprathreshold level electromagnetic stimulation.

Figures 10, 11:
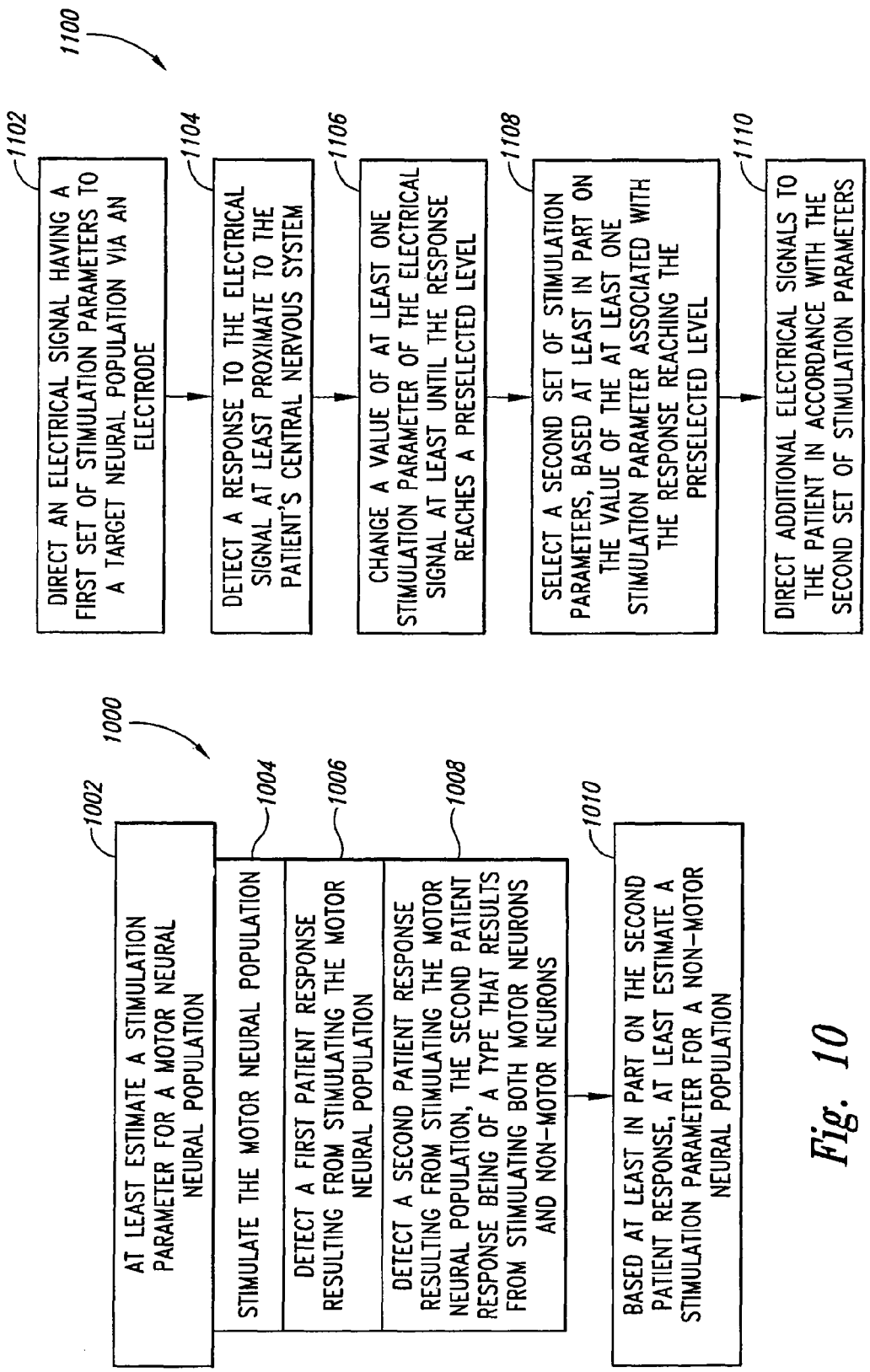
FIG. 10 is a flow chart illustrating a method for estimating a stimulation parameter for a non-motor neural population based at least in part on information from a motor neural population in accordance with another embodiment of the invention.
FIG. 11 is a flow diagram illustrating a method for providing stimulation to a patient using a set of stimulation parameters selected based at least in part on a response received from the patient's central nervous system.

The method described above with reference to FIG. 1C is directed generally to using responses obtained from stimulating a first neural population to determine stimulation parameters for stimulating a second (functionally different) neural population. FIG. 10 is a flow diagram illustrating a more specific application of such a method. The process 1000 shown in FIG. 10 can include at least estimating a stimulation parameter for a motor neural population (process portion 1002). This can include stimulating the motor neural population (process portion 1004) detecting a first patient response resulting from the stimulation (process portion 1006), and detecting a second patient response, also resulting from stimulating the motor neural population (process portion 1008). The second patient response can be of a type that results from stimulating both motor neurons and non-motor neurons. Based at least in part on the second patient response, the method can further include at least estimating (in particular embodiments, determining and/or selecting) a stimulation parameter for a non-motor neural population (process portion 1010).

In a particular application of the process 1000, stimulating the motor neural population can include applying electrical stimulation to a neural population located at the primary motor cortex. Detecting a first patient response resulting from stimulating the motor neural population can include detecting evidence that the stimulation has met or exceeded the level required for activation of the neural population. For example, detecting the first patient response can include observing or measuring a muscle action by the patient. Detecting the second patient response can include detecting a physiological characteristic that is shared by the first and second neural populations, for example, detecting a change in cerebral blood flow or other hemodynamic quantity, or detecting an electrical signal emitted by the motor neural population. The second patient response can be generally simultaneous with the first patient response (or at least clearly linked with the first patient response). For example, if it is determined that the cerebral blood flow changes by a certain amount (or has a certain value) when the motor neuron is stimulated at a current and/or voltage sufficient to produce an action potential, this information can be used to provide similar stimulation to the non-motor neural population. Accordingly, the non-motor neural population may not exhibit a response similar to the first patient response, but may exhibit the second patient response. By correlating the second patient response with the first patient response using the motor neural population, the non-motor neural population can be stimulated in a manner at least correlated with (and in some cases, generally similar to) that of the motor neural population, without requiring the non-motor neural population to exhibit the first patient response (e.g., the muscle action). In other embodiments, a generally similar approach can be followed, using different neurons to generate the first patient response. For example, sensory neurons can be stimulated to generate a first patient response that includes a sensation by the patient. The second patient response can be generally the same as any of those described above (e.g., a hemodynamic response).

FIG. 11 is a flow diagram illustrating a method 1100 for treating a patient in accordance with another embodiment of the invention. The method 1100 can include directing an electrical signal having a first set of stimulation parameters to a target neural population via an electrode (process portion 1102). The method can further include detecting a response to the electrical signal at least proximate to the patient's central nervous system (process portion 1104). For example, process portion 1104 can include detecting a hemodynamic response, electrical response, or other response at the patient's brain or other portion of the patient's central nervous system. In process portion 1106, a value of at least one stimulation parameter of the electrical signal is changed at least until the response reaches a preselected level. For example, a spatial, temporal, and/or waveform (e.g., polarity, current, voltage, pulse width, or pulse repetition frequency) parameter of the electrical signal can be varied to achieve a preselected response level. The response level can correspond to a threshold level in some embodiments, and in other embodiments, can correspond to a subthreshold level or a suprathreshold level. In process portion 1108, a second set of stimulation parameters is selected, based at least in part on the value of the at least one stimulation parameter associated with (e.g., occurring at the same time as) the response reaching the preselected level. Accordingly, the response to the electrical signal provided with the first set of stimulation parameters can influence the choice of a second set of stimulation parameters, which is then used to direct additional signals to the patient (process portion 1110). The additional signals can be directed to the same target neural population, and/or to a different neural population.

The technique described above with reference to FIG. 11 can be used to determine stimulation parameters for non-motor, non-sensory and/or other silent neurons, and in certain embodiments, parameters for motor and/or sensory neurons as well. For example, the preselected level can be determined based on stimulation levels obtained from motor or sensory neurons, (as described above with reference to FIG. 10), or can be based upon data indicating improved functionality at that preselected level for other similarly situated patients. Accordingly, the preselected level need not be obtained from motor or sensory data. In another embodiment, the foregoing method may also be applied to motor or sensory neurons during the course of therapies directed at treating such neurons, without the need for monitoring an externally exhibited patient response when a threshold simulation level is achieved. Instead, a practitioner can refer to existing data corresponding to the selected level, or can identify a level, transition, shift, "jump" or other change in a parameter that is correlated with a desired change in patient functionality. For example, the practitioner can observe a change in a hemodynamic quantity that, for a particular patient, or over a multipatient population, has been associated with patient improvement and is therefore appropriate as a stimulation parameter.

Figure 12:
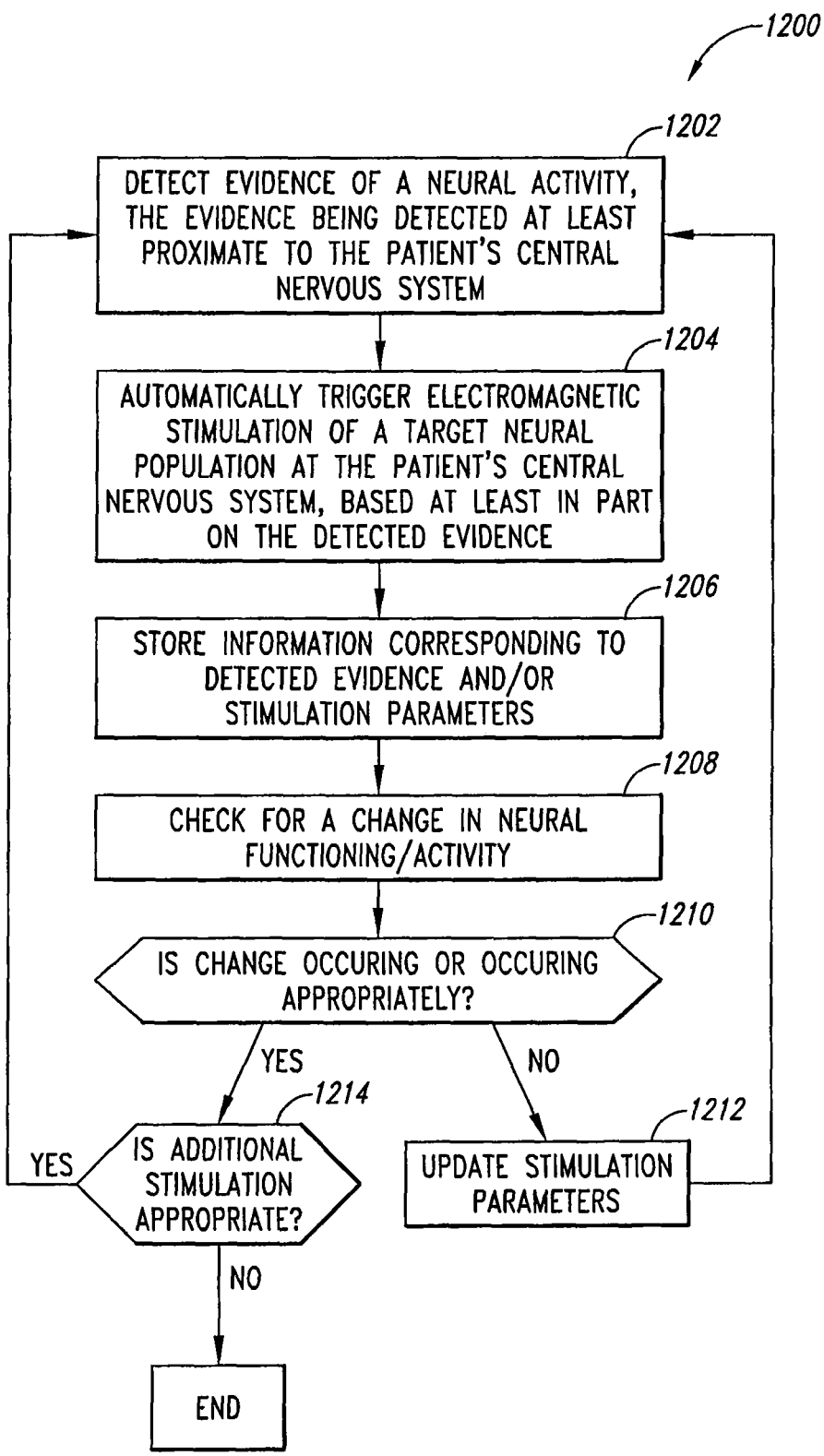
FIG. 12 is a flow diagram illustrating a method for automatically triggering electromagnetic stimulation based on evidence detected at least proximate to the patient's central nervous system in accordance with yet another embodiment of the invention.

FIG. 12 is a flow diagram illustrating a process 1200 for providing electromagnetic stimulation to a patient. Process portion 1202 can include detecting evidence of a neural activity, with the evidence being detected at least proximate to the patient's central nervous system. In process portion 1204, electromagnetic stimulation of a target neural population at least proximate to the patient's central nervous system is automatically triggered, adjusted, interrupted, resumed, or discontinued, based at least in part on the detected evidence. For example, any of the foregoing techniques relating to hemodynamic properties and/or neuroelectric properties (e.g., EEG or electrocorticographic (ECoG) signals) can provide evidence of a neural activity, and once the neural activity is detected, electromagnetic stimulation can automatically be triggered, adjusted, interrupted, resumed or discontinued. In certain cases, triggering or adjusting electrical stimulation may aid patients whose level of neural functioning is such that at least some neural activity is generated by the patient when the patient undertakes or attempts to undertake a neural task. When such neural activity is detected, the automatically generated electromagnetic stimulation may be provided at a level that affects neural membrane potentials in a manner that at least makes the generation of action potentials by a target neural population more likely, such that weak or relatively weak intrinsic neural signals have a greater chance of triggering a corresponding neural function, thereby subserving neurofunctional development (e.g., by one or more biological mechanisms associated with neuroplasticity). The automatically generated electromagnetic stimulation may result in an immediate and/or long lasting improved level of neural functioning. Because the process of providing the stimulation is automated, neither the patient nor a practitioner need take any action beyond the patient generating some level(s) of neural activity. In particular embodiments, an initial level of neural activity can correspond to the patient's attempt to engage in a physical or cognitive activity. While the patient's mere attempt may not by itself be enough to generate the desired movement or cognition, the attempt in combination with the automatically triggered stimuli is expected to be enough to do so.

In further particular embodiments, the process 1200 can include storing information corresponding to the detected evidence and/or the stimulation levels (process portion 1206). This information can be used by the practitioner to track parameters associated with the stimulation (e.g., how often the stimulation is triggered, and what characteristics the stimulation signals have). The process can also include checking for a change in neural function and/or activity (process portion 1208). In process portion 1210, it can be determined whether the change is occurring, or if it is occurring, whether it is occurring appropriately (e.g., at the appropriate pace and/or in the appropriate direction). If not, the stimulation parameters can be updated (process portion 1212) and the method can return to process portion 1202. In a particular embodiment, this feedback process can be used to identify changes or drifts in the patient's threshold stimulation levels over the course of a treatment regimen, and can automatically update the stimulation parameters accordingly. If the change is occurring appropriately, the process can further include checking to see if additional stimulation (with the existing stimulation parameters) is appropriate (process portion 1214). If so, the process returns to process portion 1202. If not, the process can end.

In at least some embodiments, process portion 1202 can include detecting hemodynamic properties that tend to change in response to changes in the patient's neural activity level(s). In many cases, an increase in perfusion levels can indicate a (desirable) increase in brain activity levels. However, this is not always the case. For example, some neuropsychiatric disorders (e.g., attention deficit disorder) can be accompanied by hyperperfusion in particular brain areas. Conversely, other neuropsychiatric disorders (e.g. depression) and some types of neuropsychiatric or cognitive dysfunctions may be indicated by hypoperfusion of a target neural area, and in still other disorders, a patient's brain may exhibit hypoperfusion in certain neural regions and hyperperfusion in other neural regions. Accordingly, effective therapy may be detected by noting or detecting a desirable or undesirable perfusion condition in one or more target neural populations. Effective treatment (e.g., provided by electrical stimulation, possibly in association with an adjunctive therapy such as behavioral therapy and/or drug therapy) may shift perfusion levels in particular target neural populations toward more normal or desirable levels. In some cases, the foregoing effects may be hidden or partially hidden by medications the patient takes, because such medications may directly or indirectly affect a neural population under consideration. Accordingly, one technique for detecting evidence of neural activity can include performing a check on a neural activity level after the patient has ceased taking a drug, as the effects of the drug wear off, and/or after the drug has worn off and the patient has returned to a "drug-off" state.

In some cases detecting evidence of neural activity can include detecting a particular value of a parameter (e.g., blood flow volume or oxygen content) that corresponds to an activity level. In other embodiments, detection includes detecting a change, rather than a particular value, of the parameter. The nature of these changes may be specific to individual patients, and/or may vary with the patient's condition. For example, changes may be quantitatively and/or qualitatively different for patients of different ages.

Figure 13:
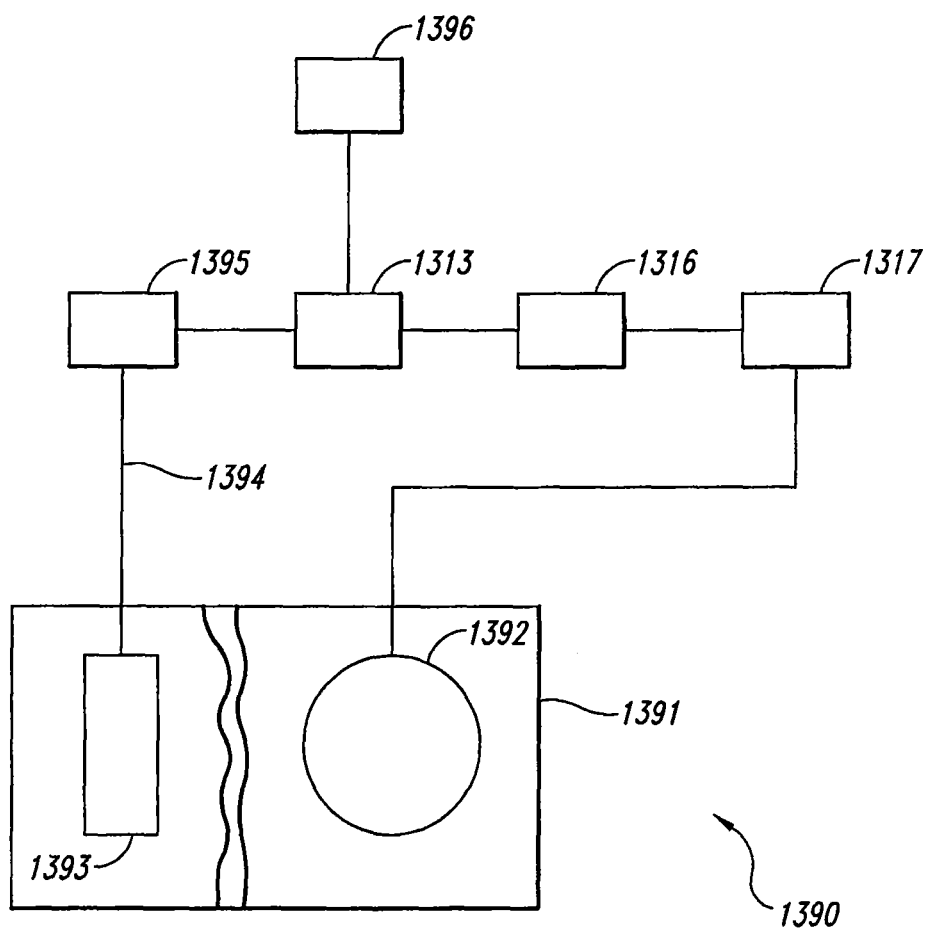
FIG. 13 is a partially schematic illustration of a device that includes both a detector and a stimulator for a patient's central nervous system.

FIG. 13 is a schematic illustration of an implantable stimulation and monitoring interface 1390 configured for stimulating a target neural population and detecting signals corresponding to neural activity according to an embodiment of the invention. Accordingly, embodiments of the interface 1390 can be used to carry out the process 1200 described above with reference to FIG. 12. Some or all aspects of the interface 1390 shown in FIG. 13 can be incorporated into any of the devices described above with reference to FIGS. 3-7. In one embodiment, the stimulation and monitoring interface 1390 comprises a support member 1391 carrying at least one stimulating element 1392 and at least one monitoring element 1393. The stimulating element 1392 may include one or more electrodes organized in accordance with a particular pattern, and the monitoring element 1393 may include a set of electrodes and/or a monitoring device positioned proximate or adjacent to the stimulating element 1392. In a particular embodiment, the stimulating element 1392 and the monitoring element 1393 can have a fixed relationship to each other. Accordingly, the interface 1390 can stimulate and monitor the same neural population, or stimulate one neural population and detect a response at another neural population spaced apart by the fixed distance. In another embodiment, these elements can be separate from or movable relative to each other (e.g., carried by different structures or support members), as indicated by broken lines, so that the practitioner has greater flexibility in selecting a set of neural populations for stimulation and one or more other neural populations for response detection. In a further aspect of this embodiment, one element (e.g., the stimulating element 1392) can be implanted to stimulate a particular neural population, and the other element (e.g., the monitoring element 1393) can be located external to the patient (e.g., at the patient's scalp) to monitor the same or a different neural population.

A lead or link 1394 may couple the monitoring element 1393 to a sensing unit 1395. The sensing unit 1395 may in turn be coupled to a controller 1313, pulse generator 1316, and pulse transmitter 1317, which are coupled back to the stimulating element 1393. Accordingly, the monitoring element 1393 can detect signals indicative of neural activity associated with particular neural populations and, via the controller 1313, can direct the stimulating element 1392 to deliver or apply stimulation signals to the same or a different target neural population. Information corresponding to the sensed data and/or the stimulation data can be stored at a memory device 1396 or other computer-readable medium (e.g., an implanted memory and/or external memory or disk drive). Aspects of some or all of the foregoing functionalities can reside on programmable computer-readable media.

In a particular embodiment, the monitoring element 1393 may include an array of cortical sensing electrodes, a deep brain electrode, and/or one or more other electrode types. In other embodiments, the monitoring element can include devices generally similar to those described above for monitoring hemodynamic quantities (e.g., optical spectroscopy monitors, cerebral blood flow monitors, cerebral blood volume monitors, Doppler flowmetry monitors, and/or others).

In some embodiments (e.g., when the monitoring element monitors electrical signals), the delivery of stimulation signals to a target neural population may interfere with the detection of signals corresponding to neural activity. As a result, the controller 1313 and/or the pulse system 1316 may periodically interrupt a neural stimulation procedure, such that during stimulation procedure interruptions, the sensing unit 1395 may analyze signals received from the monitoring element 1393. Outside of such interruptions, the sensing unit 1395 may be prevented from receiving or processing signals received from the monitoring element 1393. In particular embodiments, stimulation pulses may be interleaved with sensing "windows" so that the stimulation and monitoring tasks may be performed in alternating succession. In other embodiments, the sensing unit 1395 may compensate for the presence of stimulation signals, for example, through signal subtraction, signal filtering, and/or other compensation operations, to facilitate detection of neural activity or evidence of neural activity simultaneous with the delivery of stimulation signals to a target neural population.

In embodiments in which a neural stimulation procedure is periodically interrupted to facilitate detection of neural activity or evidence of such activity, the interface 1390 may include a single electrode arrangement or configuration in which any given electrode element used to deliver stimulation signals during the neural stimulation procedure may also be used to detect neural activity during a neural stimulation procedure interruption.

Figure 14:
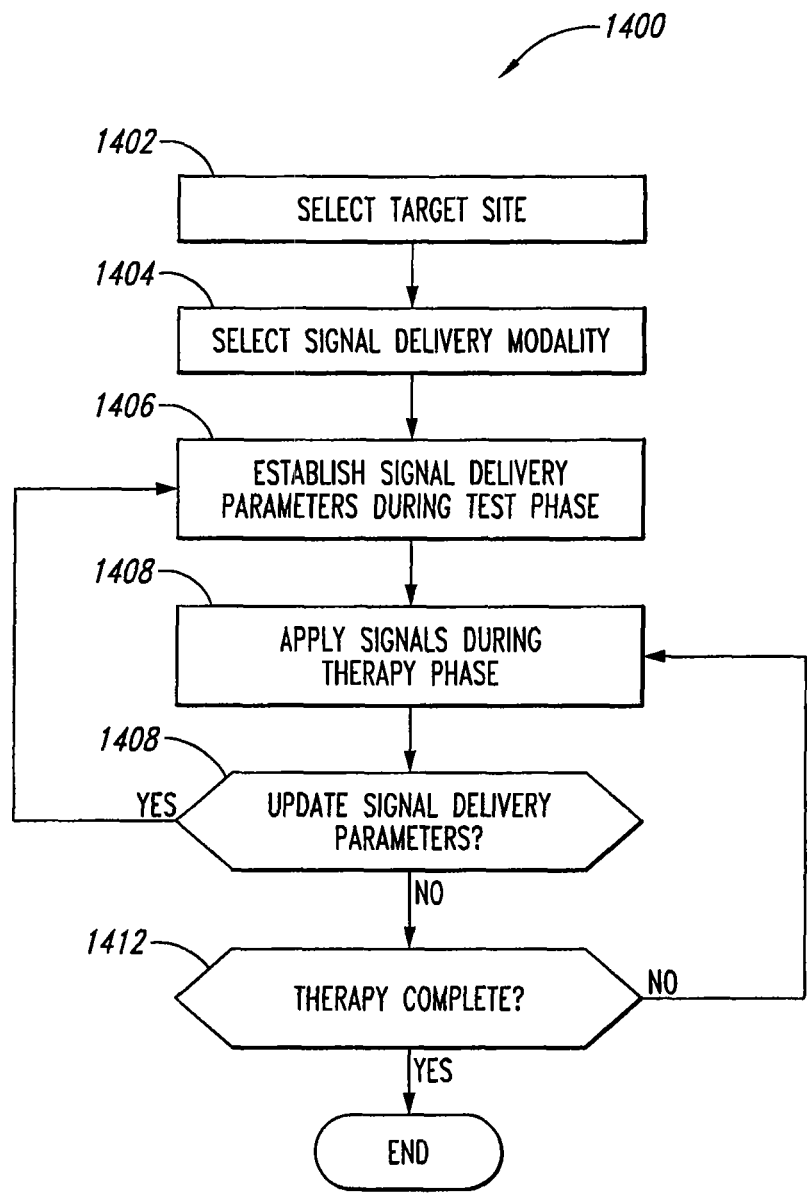
FIG. 14 is a flow diagram illustrating an overall method for treating a patient in accordance with another embodiment of the invention.

FIG. 14 illustrates a process 1400 for treating a patient, including process portions for establishing, approximating, or estimating signal delivery parameters, and applying electromagnetic signals to the patient in accordance with the established parameters. Process portion 1402 includes selecting at least one target site (e.g., a target neural population) to which electromagnetic signals will be delivered. The target site can include the dorsolateral prefrontal cortex (DLPFC), for example, if the dysfunction to be treated includes depression. In other embodiments, the target site can include other regions of the brain, or more generally, the central nervous system. In process portion 1404, a signal delivery modality is selected. The signal delivery modality can include transcranial magnetic stimulation (rTMS), transcranial direct current stimulation (tDCS), direct cortical stimulation via an implanted electrode, and/or others. In process portion 1406, signal delivery parameters are established during a test phase. For example, the current level, voltage level, or other parameter of the applied signal can be established by determining the effect of a variety of different signal levels or parameter values on the patient's memory functions. Further details of this process are described later with reference to FIG. 15.

In process portion 1408, signals are applied during a therapy phase, typically in accordance with the signal delivery parameters established in process portion 1406. In process portion 1410, it is determined whether the signal delivery parameters should be updated, as part of an overall treatment regimen. For example, process portion 1410 may include determining that the initially established signal delivery parameters have become less effective or are no longer effective. Such a determination may be made by observing increased symptoms associated with the patient's dysfunction. In some cases, the patient may become less sensitive to the signals e.g., as a result of habituation or other changes in neural response, including a change in a threshold or activation level for a neural population. In other cases, the patient may become more sensitive to the stimulation. In either type of case, if the signal delivery parameters are to be updated, process portion 1406 is repeated and additional therapy signals are then applied in process portion 1408.

In process portion 1412, it is determined whether the therapy regimen is sufficient or complete, possibly in view of therapeutic results relative to one or more time periods. For example, if the patient exhibits an expected or better than expected improvement in functions targeted by the applied electromagnetic signals, the therapy can be interrupted or halted. If not, the process can return to process portion 1408 to apply additional electromagnetic signals to the patient. Further details of particular implementations of the foregoing process are now described with reference to FIG. 15.

Figure 15:
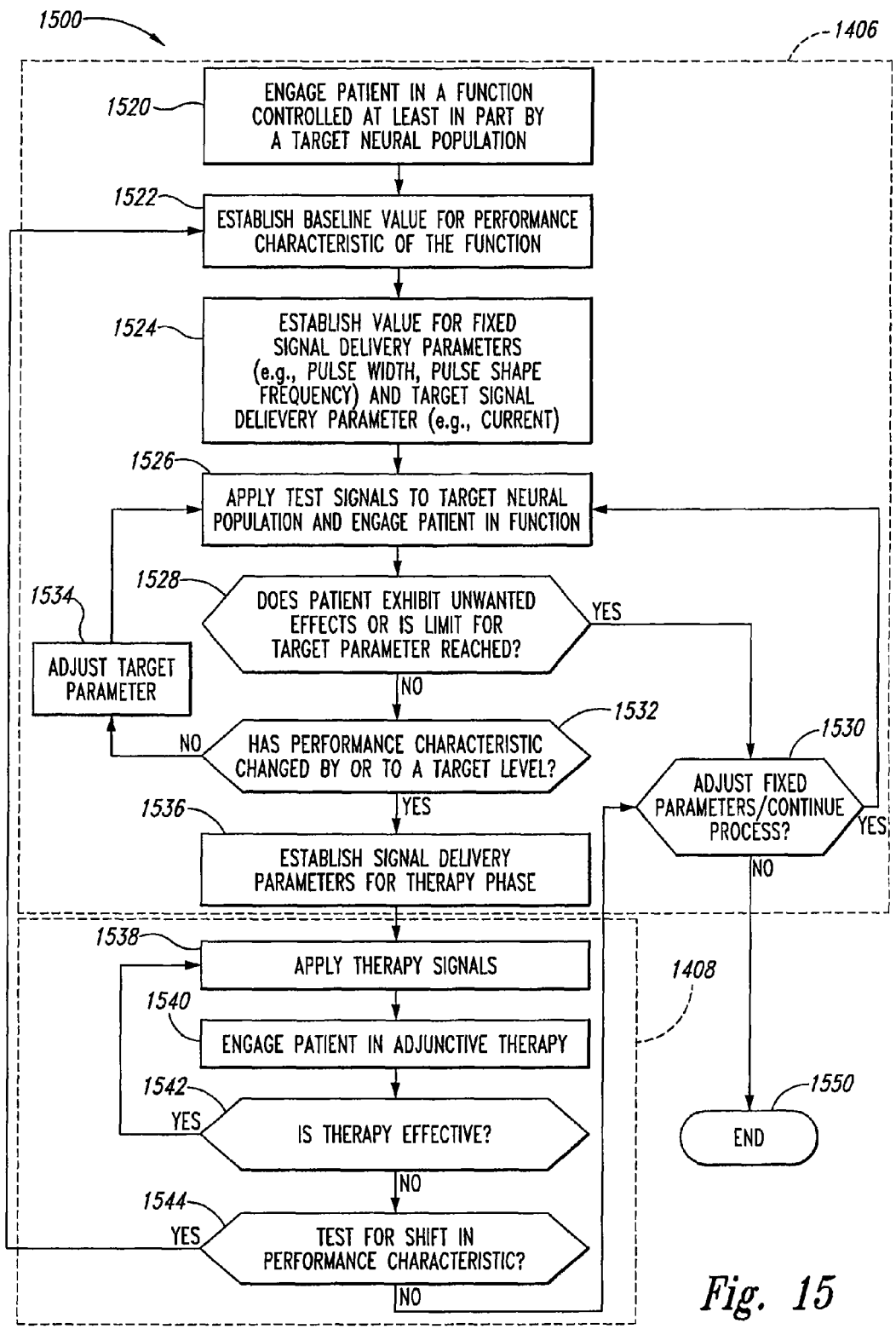
FIG. 15 is a flow diagram illustrating further details of a particular process generally outlined in FIG. 14.

FIG. 15 illustrates a process 1500 for treating a patient exhibiting a dysfunction associated with a neural population that typically does not produce directly evoked or observable motor responses, sensations, and/or other patient-reportable responses (e.g., silent neurons). One such dysfunction is depression, but the process can be applied to other dysfunctions including, but not limited to post-traumatic stress disorder (PTSD) and other psychological and/or cognitive disorders. The process 1500 generally includes process portion 1406 (establishing signal delivery parameters during a test phase) and process portion 1408 (applying signals during a therapy phase) described generally above with reference to FIG. 14. Further details of particular techniques for carrying out each of these general processes are described below.

Process portion 1520 includes engaging the patient in a function controlled at least in part by a target neural population. The function can include a cortical and/or subcortical function, e.g., a cognitive function and/or an emotional function. Particular examples of the functions included in process portion 1520 include performing a working memory task, a recognition task, a context or set switching task, a standardized "weather prediction" task, an inhibition task, a mathematical test or task, a verbal test or task, an analytical reasoning task or game, and/or other task involving executive cognitive function(s). A function included in process portion 1520 may additionally or alternatively involve evoking a particular emotion. Representative standard tests include the Paced Visual Serial Addition Test (PVSAT), Stroop test, and phonetic fluency tests. In any of these embodiments, the function is typically one that includes a volitional response on the part of the patient (e.g., thinking of a response to a query or providing an answer to a question or problem). The test can be computer-based. For example, the test can be embodied in a computer-readable medium and administered to the patient via an interactive computer program. The program can be executed on a desktop, laptop, or other computer system, which typically includes a display device, a user input device, and a graphical user interface. The computer program may further process, transfer (e.g., to another computer system coupled to a network, such as the Internet), or analyze test results. The feedback (e.g., test results) can be quickly provided to the practitioner, who can then determine the next step(s). In a particular embodiment, working memory is selected as the cortical function when the patient suffers from depression because the same general area of the brain (e.g., the DLPFC) is associated with both working memory and depression. In other embodiments, the practitioner can engage the patient in other tasks if the patient suffers from depression, or if the patient suffers from other dysfunctions. The target neural population(s) may also be different in such cases. For example, a target neural population may include one or more portions of the orbitofrontal cortex (OFC), the ventrolateral prefrontal cortex (VLPFC), the temporal pole, the pars triangularis, the superior temporal sulcus, the secondary somatosensory cortex, the secondary auditory cortex, the secondary visual cortex, Wernicke's area, the parietal association cortex, the cingulate cortex, the amygdala, the basal ganglia, the thalamic nuclei, and/or other areas not directly associated with evoking patient movements or sensations. Particular target neural populations may be defined or targeted based upon an appropriate cortical function and correspondingly placed or applied electromagnetic signals.

In process portion 1522, a baseline value is established for a performance characteristic of the function. The baseline value can be used as a point of comparison to determine the effect of electromagnetic signals applied to the patient in subsequent steps. The characteristic can be one of several characteristics associated with the patient's performance of the function. Accordingly, the nature of the characteristic may depend upon the particular function the patient performs. While the characteristic is described generally herein as a single characteristic, it will be understood that the practitioner may evaluate several characteristics and establish a baseline value for each characteristic or an aggregate baseline value as part of this step. In at least some embodiments, the characteristic can relate directly to the function the patient performs. For example, the characteristic can include a speed with which the patient performs the function, or a level of accuracy with which the patient performs the function. In other embodiments, the characteristic can be less directly related to the function itself. For example, the characteristic can include the patient's mood (e.g., sad and/or anxious) while performing the function. The patient may carry out the function multiple times (e.g., three times) and the results averaged to establish the baseline characteristic(s), or the patient can carry out the function just once.

Process portion 1524 includes establishing initial values for signal delivery parameters, including (a) fixed signal delivery parameters and (b) a target signal delivery parameter. The signal delivery parameters can include characteristics of the waveform with which electrical signals are applied to the patient, including pulse width, pulse shape, frequency, current amplitude and/or voltage amplitude. For purposes of discussion, the fixed parameters are parameters that are (at least initially) held constant while the target parameter is varied. As discussed further below, the fixed parameters can be updated, as needed, as part of the overall process. The target parameter can be selected to include the signal delivery parameter expected to be most closely correlated with a "threshold" level for the target neural population. In many cases, it is expected that the target parameter will be signal intensity, and in particular embodiments, the current amplitude or current density of the applied signal. Accordingly, the current or current density can be varied, while other fixed waveform parameters, (e.g., pulse width, pulse shape, and frequency) are held constant. The current can be varied by adjusting the output current (and/or temporal signal delivery parameters in view of delivering a particular amount of current in a given time period) of an implanted pulse generator or other signal delivery device. The current density can be adjusted by varying the area over which the applied current is directed. For example, if the patient receives electrical signals via implanted cortical electrodes, the same level of current can be distributed over an increased number of electrodes to reduce overall current density, or the current can be distributed over a reduced number of electrodes to increase the current density. Other representative target parameters include signal power and/or voltage level. In any of these embodiments, the initial value established for the target parameter may be selected to be below or well below the expected value at which the patient's ability to perform the cortical function changes, e.g., below the threshold level for the target neural population. In a representative case, the initial current value is selected to be 2 mA, applied to a particular configuration (e.g., a paired arrangement) of electrodes.

In process portion 1526, test signals are applied to the patient in accordance with the initial values established for the fixed signal delivery parameters and the target signal delivery parameter. The test signals can be applied in association or conjunction with the patient performing the function (e.g., the cognitive and/or emotional function). For example, in some cases the test signals are applied simultaneously with the patient performing the function. In other cases, these two steps may be performed sequentially. For example, the patient may first receive the test signals and then perform the function.

Process portion 1528 includes determining (a) whether the patient exhibits unwanted effects as a result of the test signals, and/or (b) whether a limit for the target parameter has been reached. The unwanted effects can include seizure activity (e.g., focal seizure and/or tonic-clonic seizure), unacceptable sensations, speech impairment or others. The patient can be monitored visually to determine whether seizure activity is exhibited, or the practitioner can use EEG, ECoG, motion sensors, and/or other feedback techniques to identify seizure activity and/or incipient seizure activity. Other unwanted effects can be monitored by the practitioner and/or reported by the patient.

The practitioner can also determine whether a limit for the target parameter has been reached (e.g., a current limit of about 6.5 mA). For example, if the current exceeds a pre-established limit, then the condition established in block 1528 is met. If, in block 1528, the practitioner identifies either unwanted effects or an indication that the target parameter limit has been reached, then process portion 1530 includes determining whether the baseline parameters should be adjusted and/or whether to continue the process. For example, the practitioner may continue with a lower current (e.g., 2.0 mA or 50% below the level at which the unwanted effect arose), if the practitioner believes that a therapeutic effect may still result at such current levels. If it is determined that the process should not be continued for any reason (e.g., if the patient suffers unwanted effects and it is believed that changing the baseline and/or target parameters will have no ameliorative effect without unacceptably affecting or curtailing an intended therapeutic effect), then the process ends (process portion 1550). Accordingly, the function performed in block 1530 can include a screening function during which the practitioner determines whether the patient is a suitable candidate for continued treatment.

If, on the other hand, it is determined that adjusting one or more of the fixed parameters may change the patient's response, then the process returns to process portion 1524 for an update of the fixed parameters. For example, if the practitioner selects applied current as the target parameter and frequency as one of the fixed parameters, and the patient exhibits unwanted effects or the current limit is reached, the practitioner may determine or believe that changing the frequency will either reduce the patient's likelihood for incurring unwanted effects or increase a likelihood of detecting or measuring an intended effect (e.g., an effect upon an aspect of task performance). In such a case, the practitioner can adjust the frequency in process portion 1524, and repeat process portions 1526 and 1528. Depending upon embodiment details, the practitioner may vary other parameters such as pulse width, pulse bursting pattern, or signal polarity.

If in process portion 1528, the patient does not exhibit unwanted effects and the limit for the target parameter has not been reached, then in process portion 1532 it is determined whether the performance characteristic has measurably or noticeably changed, for example, by a target level or to a target level. For example, if the patient exhibits a statistically significant change (e.g., $p<0.05$) relative to a set of baseline performance measures, then the condition identified in block 1532 is met. Additionally or alternatively, if the patient scores below a pre-established value on a working memory task, or if the patient's performance of the working memory task decreases by a given percentage, then the condition identified in block 1532 is met. In such cases, the process continues at process portion 1536 with establishing the signal delivery parameters for the therapy phase (process portion 1408), based at least in part on the value of the target parameter associated with the target level change in the performance characteristic. For example, if the practitioner determines that the accuracy with which the patient performs a working memory task falls below a target level when the applied electromagnetic signal has a particular current value, then the value can be considered a "threshold" value. The practitioner can then select the current level for further therapy to be below the threshold value. In particular embodiments, the current value can be selected to be from about 10% to about 95% of the threshold value and in particular embodiments, greater than 25%, 50%, or 75% of the threshold value. In other embodiments, the current value can be selected at a given increment (e.g., 0.5, 1.0, 1.5, or 2.0 mA) below the threshold value.

If in process portion 1532, the performance characteristic has not changed by or to a target degree or level, the target parameter is adjusted in process portion 1534. The test signals are then applied to the patient at the new parameter level in process portion 1526, and the cycle is repeated until either the performance characteristic does change by or to a target level (process portion 1532) or the process stops (process portion 1550). In various cases, it is expected that a threshold level will be associated with a decrease in patient performance. In such cases, threshold testing can begin with the application of a low current level, and the current level can be increased until the patient's performance falls by or to a selected level, which may be expected to be indicative of the threshold current level. In some instances, the patient's performance of a given task may not change monotonically or unidirectionally as a function of adjustments to the target parameter. For example, as the current level applied to the patient increases during early portions of the test phase 1406, the patient's performance of a working memory task or other task (e.g., reaction time) may actually improve. In some cases, the improvement in memory or other function may indicate that at least certain relevant neural circuits are activated, and can thus correspond to a threshold level of the target neural population. In the event that a performance improvement is detected or measured, the practitioner may continue to increase the current level to identify a signal intensity level at which performance declines.

Once the signal delivery parameters are established in process portion 1536, the actual therapy is conducted in process portion 1408. Process portion 1408 includes applying therapy signals (process portion 1538) and, optionally, engaging the patient in one or more adjunctive therapies (process portion 1540). In general, the therapy signals are based upon or determined in accordance with at least one threshold level. The therapy signals are generally expected to be unipolar to treat cognitive, emotional, neuropsychiatric and/or neuropsychological disorders, though in some instances the therapy signals may be bipolar at one or more times. In some instances, the beneficial effect to the patient may last only as long as the treatment regimen lasts. In other instances, the patient may achieve long-lasting benefits that extend significantly (e.g., by weeks, months or years) beyond the term of the treatment regimen. In some of these latter instances, the electromagnetic signals may facilitate a neuroplastic response by the patient, and in still further particular embodiments, unipolar signals applied in accordance with a given polarity may be supplemented with unipolar signals applied in accordance with the opposite polarity and/or bipolar signals, where such signals may be expressly directed at facilitating a lasting response. Depending upon embodiment details, separate threshold levels may be determined in one or more manners described herein for anodal unipolar, cathodal unipolar, or bipolar signals. Therapeutic signal levels may be accordingly established based upon therapy signal polarity in view of a corresponding polarity-specific threshold level.

The optional adjunctive therapy can include psychotherapy, counseling, cognitive behavioral therapy, visualization or meditation exercises, hypnosis, memory training tasks and/or other techniques that, in addition to the electromagnetic signals, are expected to reduce or eliminate the patient's neural dysfunction. Therapeutic signal parameters (e.g., signal polarity, amplitude, or frequency) applied in association with a given adjunctive therapy may be the same as or different from therapeutic signal parameters applied in association with a different adjunctive therapy or in the absence of an adjunctive therapy. Different therapeutic parameters in view of patient treatment during an adjunctive therapy, outside of an adjunctive therapy, or across different adjunctive therapies may be based upon identical or different threshold levels, which may be determined in one or more manners described herein.

Figure 16A:
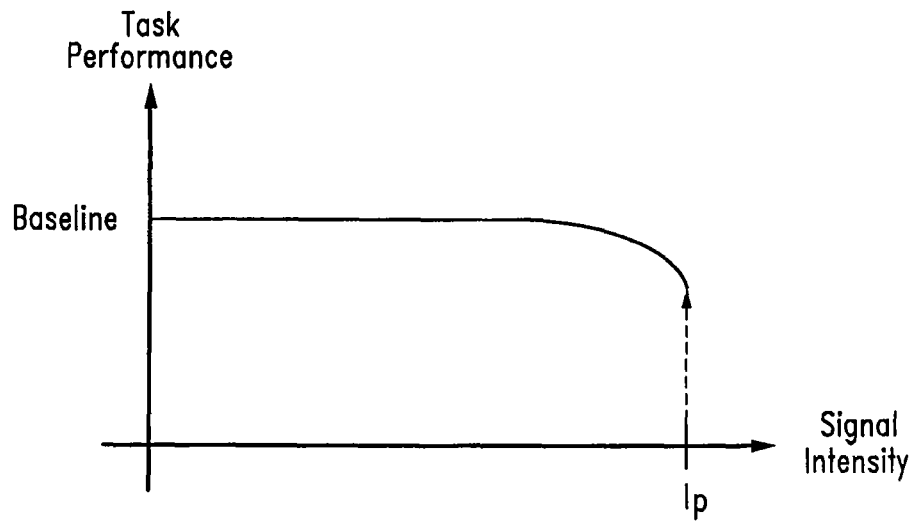
FIGS. 16A-16C graphically illustrate threshold determination techniques in accordance with embodiments of the invention.

In general, a threshold level corresponds or approximately corresponds to a lowest or near-lowest stimulation signal intensity that causes a detectable change in a patient behavior, performance, function, or state. FIG. 16A is a representative illustration of a patient performance based threshold level $I_p$ determined relative to performance degradation for a single task. In various embodiments, $I_p$ may correspond to a current level or signal intensity that gives rise to a statistically significant decline in patient task performance relative to a baseline value.

Figure 16B:
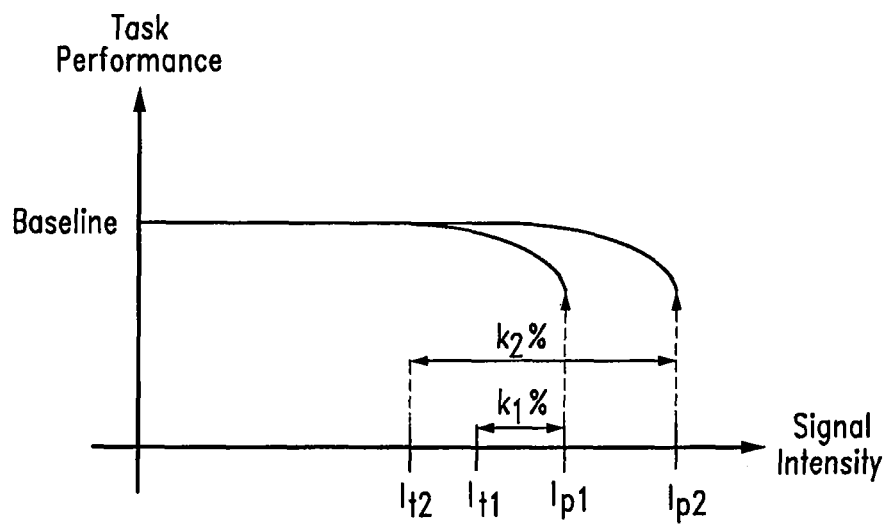

In some embodiments, more than one type of threshold level may be defined, determined, approximated, or estimated for a patient. Depending upon embodiment details, multiple therapy or treatment signal intensities may be defined, determined, or estimated based on one or more threshold signal intensities. As one example, different threshold and/or treatment signal intensities may exist when stimulation is to be applied to more than one stimulation site, such as two or more distinct cortical areas in the same or different brain hemispheres. Additionally or alternatively, as indicated above, different threshold levels may exist for different signal polarities. FIG. 16B is a representative illustration of a first performance based threshold level $I_{p1}$ determined for a first polarity configuration (e.g., anodal unipolar stimulation), and a second performance based threshold level $I_{p2}$ determined for a second polarity configuration (e.g., cathodal unipolar stimulation, or bipolar stimulation). In one embodiment, outside of a behavioral therapy session (e.g., during portions of a patient's normal day-to-day activities), patient symptoms may be treated or managed with a first therapy current level $I_{p1}$ that is approximately 75%-95% (e.g., 80%) of $I_{p1}$. During portions of a behavioral therapy session, it may be desirable to facilitate symptomatically beneficial neuroplastic changes using a second therapy current level $I_{t2}$ that is approximately 25%-75% (e.g., 50%) of $I_{p2}$.

Figure 16C:
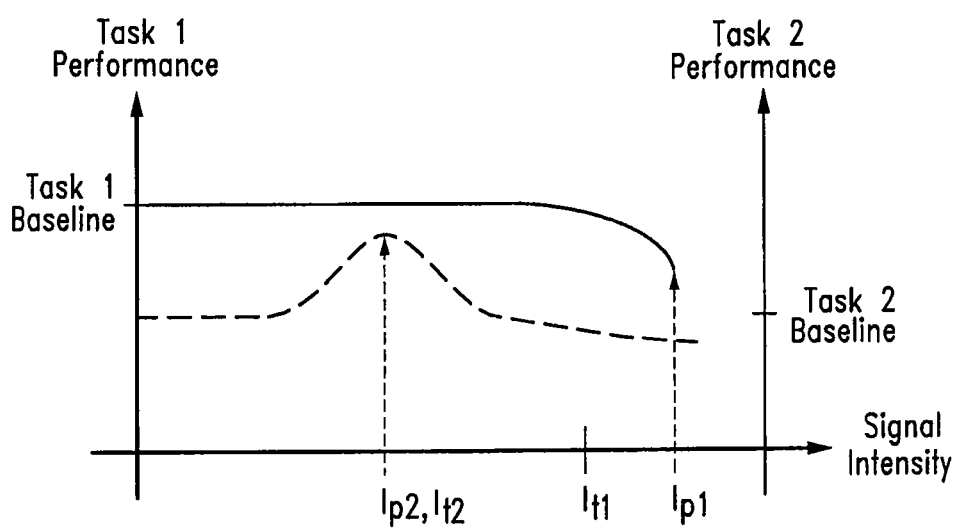

As another example, different threshold levels may be determined when a set of patient performance metrics exhibits multiple deviations of significance (e.g., performance improvement as well as performance degradation) across a range of stimulation signal parameters. FIG. 16C is a representative illustration of a first threshold level $I_{p1}$ and a second threshold level $I_{p2}$ that are associated with patient task performance degradation and patient task performance improvement, respectively. In one embodiment, $I_{p1}$ may correspond to patient performance of a first type of task (indicated by a solid line in FIG. 16C), and $I_{p2}$ may correspond to patient performance of a second type of task (indicated by a dashed line in FIG. 16C). In another embodiment, $I_{p1}$ and $I_{p2}$ may each correspond to patient performance of a single type of task.

In one embodiment, outside of a behavioral therapy session, patient symptoms may be treated or managed with a first therapy current level $I_{t1}$ that is approximately 75%-95% of $I_{p1}$. During portions of a behavioral therapy session, neuroplastic changes may be facilitated using a second therapy current level $I_{t2}$ that is approximately 25%-75% of $I_{p1}$. In the event that $I_{p2}$ falls within the range of 25%-75% of $I_{p1}$, then the second therapy current level $I_{t2}$ may equal $I_{p2}$. Alternatively, $I_{t2}$ may be defined as a given percentage (e.g., 50%) of $I_{p2}$; or $I_{t2}$ may be defined in accordance with a mathematical relationship involving $I_{p1}$ and $I_{p2}$ (e.g., $I_{t2}$ is an average of $I_{p1}$ and $I_{p2}$).

Referring again to FIG. 15, process portion 1542 includes a check to determine whether the therapy conducted thus far is effective. If so, the therapy continues (process portion 1538 and, optionally, process portion 1540). If not, it is determined whether a test should be conducted to identify a shift in the performance characteristic. For example, as discussed above, if the patient becomes adapted or habituated to the therapy signals, or if other patient conditions change in a manner that causes the initially established signal parameters to be less effective or ineffective, it may be beneficial to update or reestablish the signal delivery parameters. Part of this process can include testing the patient to see if the baseline value for the performance characteristic has shifted. For example, the patient's threshold level (in a particular case, an amount of electrical stimulation required to measurably affect or interfere with a working memory task) may shift, drift or otherwise change over the course of time, as a result of or independent of the therapy signals. In such a case, the process returns to process portion 1522 to re-establish the baseline value for the performance characteristic, and the steps described above with respect to process portions 1524-1536 are repeated. If in process portion 1544 it is determined that a test for a shift in the performance characteristic is not to be conducted, the process returns to process portion 1530. In process portion 1530, the patient is screened to determine whether any additional changes or adjustments can be made to the overall treatment regimen (e.g., changes to the baseline signal delivery parameters). If not, the process ends at process portion 1550.

One feature associated with embodiments of the processes described above generally, and in particular with reference to FIGS. 14-16C, is that they can be used to determine signal delivery parameters for applying signals to neural populations that do not typically have direct control over sensory or motor functions or responses, but instead are associated with other functions, e.g., cognition and emotion. This technique can be particularly useful for treating depression, PTSD, bipolar disorder, anxiety, craving, obsessive-compulsive disorder, Tourette's syndrome, schizophrenia, disassociative disorders, borderline personality disorder, addictive behavior, attention deficit/hyperactivity disorder (ADHD), autism, Asperger's disease, and/or other cognitive and/or psychological dysfunctions that are not primarily based in motor or sensory neural populations or which are significantly modulated by non-motor or non-sensory neural populations. Further electromagnetic signal application techniques that may be used to treat the foregoing and other patient dysfunctions using systems and methods such as those described herein are disclosed in Provisional Application 60/835,245, titled "Methods for Treating Neurological Disorders, Including Neuropsychiatric and Neuropsychological Disorders, and Associated Systems", filed Aug. 2, 2006 and incorporated herein by reference in its entirety.

An advantage of the foregoing feature is that it can be used to establish signal delivery parameters in a relatively short period of time. For example, a practitioner can much more quickly change the current applied to the patient and identify a corresponding change in the patient's performance of a memory task (which can occur in a single test therapy session), than change the current and wait to see if repeated therapy sessions result in a change in a patient's depression symptoms (which may not occur until several or many therapy sessions are completed). Accordingly, the patient's performance of a working memory task can be used to establish signal delivery parameters for treating depression, without requiring depression to be causally linked to memory (although, in some cases changes in memory may be caused by changes in the patient's depression level, with reduced depression resulting in improved memory).

In at least some ways, the relationship between testing memory and treating depression may be analogous to the relationship between testing motor movement and treating a motor dysfunction arising from, for example, a stroke. For example, applying an incrementally increasing test signal until the patient's performance of a memory task changes, in order to establish signal delivery parameters for treating depression, can be analogous to applying a corresponding type of test signal until the patient exhibits a motor response, in order to establish signal delivery parameters for treating stroke. In the first case, the ultimate therapy signals are then applied to treat depression, and in the second case, the ultimate therapy signals are applied to treat stroke.

In other ways, the test phase described above is significantly different than that used to establish the threshold for motor neurons and/or sensory neurons. In particular, threshold testing for motor neurons typically includes triggering a non-volitional, evoked motor act when a target motor neural population is electrically stimulated. Threshold testing for sensory neurons typically includes triggering an evoked sensation when a target sensory neural population is electrically stimulated. Conversely, during embodiments of the process described above with reference to FIG. 15, the patient engages in a volitional cognitive or emotional act, for example, taking a memory test, performing a mathematical task, or participating in an experience (e.g., viewing and responding to sounds or images expected to generate an emotional response) that can be affected by a stimulation signal in order to provide responses that indicate a neural threshold. Additionally, a threshold level and/or therapeutic signal intensity associated with a motor or sensory function may be similar to or different than a threshold level and/or therapeutic signal intensity associated with a cognitive or emotional function.

In particular embodiments, techniques used during the test phase 1406 of the foregoing processes are generally identical to those used during the therapy phase 1408. For example, if a particular target neural population is tested using a particular modality during the test phase, the same modality can be used to apply therapeutic signals to the same target population during the therapy phase. In other embodiments, the techniques may differ from one phase to the next. For example, a correlation can be established between the behavior of a first neural population (e.g., at the right brain hemisphere) and that of a second neural population (e.g., at the left brain hemisphere). If the second neural population is the one to which therapy signals will ultimately be directed, but the first neural population is more easily accessible, the practitioner can apply the test signals to the first neural population and use the results to screen the patient. If the patient passes the screening test, the parameter data obtained while testing at the first neural population can be applied during therapy applied to the second neural population. If the patient fails the screening test, the patient has advantageously avoided stimulation to the less accessible second neural population.

In a roughly analogous manner, a correlation can be established between a first modality (e.g., rTMS) that is relatively easy to implement without surgery, and a second modality (e.g., direct cortical stimulation with implanted electrodes), which requires generally minimally invasive surgery. Data obtained during the test phase with one modality can be applied, possibly with a transformation function or correction factor, to signals applied during the therapy phase with another modality.

In general, any of the foregoing test and therapy phases are conducted on a patient-by-patient basis. That is, the results of a test performed on one patient are used to develop signal delivery parameters for therapy applied to the same patient. While it is not generally expected that test results are transferable, in some cases, the test results obtained from one patient or patient population may be used to establish signal delivery parameters for therapy applied to another. Such instances may occur when patient dysfunctions, physiologies and responses to stimulations are expected to be well correlated or very similar.

In at least some instances, embodiments of the foregoing methods include statistical analyses to determine whether the results of a task performed by the patient receiving electromagnetic signals differ from the baseline results by an amount significant enough to indicate a threshold level. The analyses can be performed by any of a wide variety of computers, processors and/or like devices, and can be incorporated into a suitable computer-readable medium. A representative computer-implemented method for establishing patient treatment parameters in accordance with one embodiment includes receiving a set of baseline values of a characteristic with which a patient performs a function controlled at least in part by a target neural population, while the patient is not subject to external electromagnetic signals directed to the target neural population. The method can further include receiving multiple values of the characteristic with which the patient performs the function while the patient is subject to external electromagnetic signals directed to the target neural population. A statistical analysis of the multiple values is then performed, and, based at least in part on the statistical analysis, the method includes determining a probability that the patient's performance while subject to the electromagnetic signals is affected by the electromagnetic signals. In further particular aspects, the function can include a memory test, and the characteristic can include a speed or accuracy with which the test is completed. As described in greater detail below, the analysis applied to the values of the characteristic may depend upon the characteristic itself.

In a particular example, each patient performs three PVSAT test series to establish baseline performance characteristics prior to cortical stimulation (or other application of electromagnetic signals). One test series can include 80 trials, in which the subject responds correctly (success), incorrectly (failure), or with an invalid response (failure) to each of the 80 trials. These three measurements are then used to estimate the baseline probability of success. In addition, the time it takes to respond to each of the 80 trials is recorded, and the mean and standard deviation are calculated assuming a normal distribution.

After the three baseline tests are administered, at least one PVSAT test series is performed during cortical stimulation at each of the following current intensities: 2, 3, 4, 5, 6, and 6.5 mA. The probability of obtaining less than or equal to the number correct given the baseline distribution is then calculated. A probability of less than or equal to a particular value (e.g., 0.05) will indicate a small likelihood of observing the number correct during stimulation given the baseline distribution. This in turn can be used as an indication of an applied current level corresponding to a neural threshold. The mean and standard deviation of the reaction time is also calculated for each of these trials and compared with baseline data. A significant difference (e.g., $p \leq 0.05$) between the mean baseline and subsequent mean reaction times collected during stimulation can be used as an indication of an applied current level corresponding to threshold. The reaction time data can be used in conjunction with or in lieu of the accuracy data.

The foregoing data analyses are generally performed on a patient-by-patient basis (as discussed previously) in order to guide the practitioner in determining the appropriate stimulation level for each patient. Performing a single-case statistical analysis in which all the data points arise from a single patient violates the standard statistical assumption of independence of observations. In these data analyses, the non-independence of observations is ignored and statistical methods are applied in standard ways. Smaller estimates of variability are likely to be obtained in the single-case situation, as compared to variability in a larger population, since observations come from the same person. The implication of ignoring the foregoing assumption is that the distribution is expected to have less variability than that expected from a population-based distribution when used to calculate the above probabilities. However, it is expected that the results nevertheless provide statistically meaningful information to the practitioner, since one objective of these analyses is to determine a stimulation level that affects the patient's performance.

Different analyses may be applied to the accuracy of the patient's response than to the speed of the patient's response, as noted above. Beginning with accuracy, in a particular embodiment, each of the foregoing 80 trials is assumed to be a Bernoulli trial, e.g., a trial that results in one of two mutually exclusive outcomes (success or failure). The trials are assumed to be independent and the probability of a success, p, is assumed to remain constant from trial to trial. In 80 repetitions of a Bernoulli trial, the number of possible successes is 0, 1, 2, ..., 80. The statistical distribution associated with the probabilities of success is assumed to be the binomial distribution. Given the underlying baseline probability of success, the probability of observing a specific number of successes (or a lower number of successes) can be calculated using the binomial distribution.

The following equation representing the cumulative distribution function of a binomial distribution is then used to calculate the probability of observing less than or equal to a number of correct responses, ($x_i$), at a specific stimulation level i, given a subject's baseline estimate of probability of success.

$$P_i\{X \leq x_i \mid n, p\} = \sum_{j=0}^{x_i} {}_nC_j p^j (1-p)^{n-j}$$

where:
X represents the random variable of the number of correct responses during a test series;
$x_i$ is the observed number of correct responses at stimulation level i;
n=80 (number of trials in a test series);
p is the baseline probability of success estimated by the median proportion correct during baseline testing (e.g., the median proportion correct from 3 baseline PVSAT test series)

$${}_nC_j = n!/(j!(n-j)!)$$

Suitable software packages (e.g., Microsoft Excel) calculate such probabilities from the binomial distribution (e.g., using the function BINOMDIST).

A different analytical technique can be used to evaluate the patient's reaction time. In a particular example, only reaction times for correct answers are used in this analysis. Correct answer reaction times from the three baseline runs are combined, and a mean and standard deviation are then calculated for the combined data, assuming a normal distribution. The baseline mean reaction time and subsequent mean reaction times for each of the tests performed during trials with stimulation administered are then compared using standard t-tests.

A representative program can identify the following results after the patient performs the baseline trials:
Number of correct answers from each of three baseline test series;
Median proportion of correct answers from the three baseline test series; and
Mean reaction time and standard deviation associated with correct answers during the three baseline test series.

The representative program can identify the following results after the patient completes a series of trials at a particular current level:

Number of correct answers from the test series;
P-value for less than or equal to the number of correct answers based on the baseline distribution;
Mean reaction time and standard deviation for correct answers from the test series; and
P-value for the t-test of difference in mean reaction time for correct answers between baseline and each stimulation level.

The practitioner can review the foregoing results as the patient performs the test at each signal parameter (e.g., current level) setting to determine how to proceed. As discussed above, the practitioner can determine how to proceed based on any of the foregoing results either alone or in combination, or in association with any other characteristics of the patient's performance (e.g., the patient's mood), depending upon factors that include but are not limited to the patient dysfunction and the test engaged in by the patient.

From the foregoing, it will be appreciated that specific embodiments of the invention have been described herein for purposes of illustration, but that various modifications may be made without deviating from the invention. For example, in some embodiments, data obtained from a first neural population can be used to identify stimulation parameters for a second neural population of the same patient. In other embodiments, data obtained from stimulating one type of neural population in one patient can be used to at least influence the choice of stimulation parameters selected for the same or a different type of neural population in a different patient. Once stimulation parameters for a particular target neural population have been identified, a corresponding treatment regimen can include adjunctive therapies in addition to electromagnetic stimulation. Adjunctive therapies can include cognitive-based activities when the target neural population includes neurons associated with such activities, and/or other types of activities (e.g., physical therapy, auditory activities, visual tasks, speech production or language comprehension) for neurons associated therewith. Adjunctive therapies can also include drug-based therapies. Several aspects were described above in the context of current amplitude; in other embodiments, threshold may be determined as a function of voltage amplitude and/or other signal characteristics, including power. Signals can be applied to the cortex and/or below the cortical surface using any of the techniques described above. Cortical and/or other types of electrodes can include any suitable number of contacts, e.g., six as shown in FIG. 6, or other numbers including two in a particular embodiment. The statistical analyses were described above in the context of representative examples, and can be conducted in accordance with other techniques in other embodiments.

Aspects of the invention described in the context of particular embodiments may be combined or eliminated in other embodiments. For example, aspects of the automated feedback system described in the context of FIG. 13 may be combined with aspects of the stimulation devices described with reference to FIGS. 3-7. Aspects of the invention described in the context of treating particular psychiatric, psychological, and/or cognitive disorders may also be combined with the treatment of motor and/or sensory function disorders, which may be associated with stroke, traumatic brain injury, cerebral palsy, multiple sclerosis, Parkinson's disease, or other conditions. In one example, motor function rehabilitation may be facilitated using cortical stimulation applied to the motor cortex, the premotor cortex, and/or other brain area at a signal intensity between approximately 25%-75% (e.g., 50%) of an evoked motor threshold, and post-stroke depression may be treated using cortical stimulation applied to the left DLPFC and/or other brain area at a signal intensity determined in accordance with one or more techniques described herein. The motor function rehabilitation may involve an adjunctive therapy such as physical therapy, while treatment of post-stroke depression may involve counseling or another adjunctive therapy as described above. As another example, electromagnetic stimulation may be applied to the cortex and/or deep brain structures to treat symptoms of Parkinson's disease in one or more manners described in the relevant art; and cortical stimulation may be applied in one or more manners in accordance with the present invention to treat emotional or cognitive effects associated with Parkinson's disease (where such emotional or cognitive effects may arise in association with or be exacerbated by a patient's drug regimen).

While advantages associated with certain embodiments of the invention have been described in the context of those embodiments, other embodiments may also exhibit such advantages, and not all embodiments need necessarily exhibit such advantages to fall within the scope of the invention. Accordingly, the invention is not limited except as by the appended claims.

We claim:

1. A method for treating a mood and/or anxiety disorder in a patient, comprising:
    engaging the patient suffering from the mood and/or anxiety disorder in a function controlled at least in part by a target neural population;
    positioning at least one electrode below the patient's skull above the dura matter over the target neural population of the frontal lobe and applying electromagnetic signals to the target neural population via the at least one electrode;
    adjusting a target parameter in accordance with which the electromagnetic signals are applied to the patient, based at least in part on a characteristic of the patient's performance of the function;
    applying the electromagnetic signals to the patient with the adjusted target parameter;
    evaluating the patient's response to the electromagnetic signals, including the characteristic of the patient's performance; and
    based at least in part on the evaluation of the patient's response:
    (a) determining whether to apply further electromagnetic signals to the patient;
    (b) establishing a value of the target parameter for applying further electromagnetic signals to the patient; and/or
    (c) adjusting another target parameter in accordance with which the electromagnetic signals are applied to the patient,
    wherein the method further comprises:
    determining a parameter limit based at least in part on a value of the target parameter when the characteristic of the patient's performance of the function changes by or to a target level; and
    applying additional electromagnetic signals to the patient as treatment for a neurological dysfunction, with a value of the target parameter at or below the parameter limit;
    wherein the target neural population is a first target neural population, and wherein applying additional electromagnetic signals to the patient includes applying the additional electromagnetic signals to a second target neural population different than the first.

2. The method of claim 1, further comprising:
    establishing a baseline value for the characteristic by engaging the patient in the function prior to applying electromagnetic signals to the target neural population; and
    comparing the patient's response to the baseline value.

3. The method of claim 1, further comprising:
    applying therapeutic electromagnetic signals to the patient to address a patient dysfunction using a value of the target parameter based at least in part on the evaluation of the patient's response.

4. The method of claim 1 wherein applying the electromagnetic signals to the patient with the adjusted target parameter is performed simultaneously with engaging the patient in the function.

5. The method of claim 3 wherein the patient dysfunction includes depression and the function includes a memory task.

6. The method of claim 1 wherein applying electromagnetic signals with the adjusted parameter includes applying the electromagnetic signals without triggering a seizure response in the patient.

7. The method of claim 1 wherein establishing a value of the target parameter is performed on a patient-by-patient basis.

8. The method of claim 1 wherein applying electromagnetic signals includes applying anodal electromagnetic signals.

9. The method of claim 1 wherein applying additional electromagnetic signals includes applying additional electromagnetic signals to at least reduce patient depression.

10. The method of claim 9, further comprising engaging the patient in psychological counseling during a treatment regimen that includes applying additional electromagnetic signals to at least reduce the patient's depression.

11. The method of claim 1, further comprising engaging the patient in an adjunctive therapy while applying the additional signals.

12. The method of claim 11 wherein the adjunctive therapy is different than the function performed by the patient.

13. The method of claim 1 wherein determining the parameter limit includes determining a first parameter limit based on the characteristic at a first point in time prior to applying the additional signals, and wherein the method further comprises:
    determining a second parameter limit based at least in part on a value of the target parameter when the characteristic of the patient's performance of the function changes by or to the target level at a second point in time after applying the additional signals.

14. The method of claim 1 wherein applying electromagnetic signals includes applying electromagnetic signals via a first modality, and wherein applying additional electromagnetic signals includes applying additional electromagnetic signals via a second modality different than the first.

15. The method of claim 1 wherein determining whether to apply further electromagnetic signals is based at least in part on the patient's response to electromagnetic stimulation provided by a non-implanted device, and wherein applying additional electromagnetic signals includes applying the additional electromagnetic signals via an implanted electrode.

16. The method of claim 1, further comprising:
    engaging the patient in the function while the patient is not under the influence of extrinsic electromagnetic signals applied to the target neural population; and
    comparing results of the patient's performance of the function with and without the influence of electromagnetic signals applied to the target neural population.

17. The method of claim 1 wherein engaging the patient in the function includes engaging the patient in a memory task.

18. The method of claim 1 wherein engaging the patient in the function includes engaging the patient in a mathematical task.

19. The method of claim 1 wherein engaging the patient in the function includes engaging the patient in a phonetic task.

20. The method of claim 1 wherein evaluating the patient's response includes identifying a reduced level of performance.

21. The method of claim 1 wherein the characteristic includes the speed with which the patient performs the function.

22. The method of claim 1 wherein the characteristic includes the accuracy with which the patient performs the function.

23. The method of claim 1 wherein the characteristic includes the patient's mood while performing the function.

24. The method of claim 1 wherein engaging the patient in the function includes eliciting an emotional response from the patient.

25. The method of claim 1 wherein adjusting a target parameter includes adjusting an intensity with which the electromagnetic signals are applied to the patient.

26. The method of claim 1 wherein adjusting a target parameter includes adjusting a current applied to an electrode.

27. The method of claim 1 wherein adjusting a target parameter includes adjusting a current density of an electromagnetic signal applied to the patient.

28. The method of claim 1 wherein adjusting a target parameter includes adjusting a power level at which electromagnetic energy is applied to the patient.

29. The method of claim 1 wherein adjusting a target parameter includes adjusting a characteristic of an electromagnetic signal waveform applied to the patient.

30. A method for treating mood and/or anxiety disorder in a patient, comprising:
    positioning at least one electrode below the patient's skull above the dura matter over a target neural population of the frontal lobe of the patient;
    applying electromagnetic test signals to the target neural population via the at least one electrode;
    adjusting a current with which the test signals are delivered while engaging the patient in a cognitive function;
    ceasing to apply the test signals if the patient's performance of cognitive changes by or to a target level or if the patient exhibits unwanted effects;
    determining a current limit based at least in part on a value of the current when the patient's performance of the cognitive function changes by or to the target level; and
    applying electromagnetic therapy signals to the patient at a current level that is at or below the current limit;
    wherein applying electromagnetic therapy signals includes selecting the electromagnetic therapy signals to be within a first range relative to a first current limit if the current is applied with a first polarity, and selecting the electromagnetic therapy signals to be within a second range relative to a second current limit if the current is applied with a second polarity different than the first polarity, the second range being different than the first range.

31. The method of claim 30 wherein determining a current limit includes comparing the patient's performance of the cognitive function with and without applying electromagnetic signals to the target neural population.

32. The method of claim 30 wherein applying electromagnetic signals includes addressing patient depression, and wherein cortical function includes a memory task.

33. The method of claim 30 wherein engaging the patient in the cognitive function includes engaging the patient in a memory task.

34. The method of claim 30 wherein engaging the patient in the cognitive function includes engaging the patient in a mathematical task.

35. The method of claim 30 wherein determining a current limit includes identifying a speed with which the patient performs the cognitive function and comparing the speed to a baseline value.

36. The method of claim 30 wherein determining a current limit includes identifying an accuracy with which the patient performs the cognitive function and comparing the accuracy to a baseline value.

37. The method of claim 30 wherein determining a current limit includes identifying a mood with which the patient performs the cognitive function and comparing the mood to a baseline mood.

38. The method of claim 30 wherein ceasing to apply the test signals is triggered by the patient exhibit seizure activity.

* * * * *